United States Patent
Kortenbach et al.

(10) Patent No.: US 8,066,721 B2
(45) Date of Patent: Nov. 29, 2011

(54) SURGICAL CLIP APPLICATION ASSEMBLY

(75) Inventors: Juergen A. Kortenbach, Miami Springs, FL (US); Robert Sixto, Jr., Miami, FL (US); Kevin W. Smith, Coral Gables, FL (US); Charles Slater, Fort Lauderdale, FL (US); Saul Gottlieb, Miramar, FL (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 598 days.

(21) Appl. No.: 11/728,536

(22) Filed: Mar. 26, 2007
(Under 37 CFR 1.47)

(65) Prior Publication Data
US 2007/0265640 A1  Nov. 15, 2007

Related U.S. Application Data

(60) Division of application No. 10/010,247, filed on Dec. 6, 2001, now Pat. No. 7,232,445, and a continuation-in-part of application No. 09/931,528, filed on Aug. 16, 2001, now Pat. No. 6,569,085, and a continuation-in-part of application No. 09/891,775, filed on Jun. 25, 2001, now Pat. No. 6,716,226, and a continuation-in-part of application No. 09/730,911, filed on Dec. 6, 2000, now Pat. No. 6,551,315.

(60) Provisional application No. 60/292,419, filed on May 21, 2001.

(51) Int. Cl.
*A61B 17/10* (2006.01)

(52) U.S. Cl. ............................. 606/142; 606/208
(58) Field of Classification Search .............. 606/139, 606/142, 143, 159, 207, 208, 205, 206; 81/342, 81/345, 346, 347, 348, 381, 350, 351, 383, 81/65.2, 362, 376, 383.5
See application file for complete search history.

(56) References Cited

U.S. PATENT DOCUMENTS 266,632 A  10/1882  McCormick
268,632 A  12/1882  Danforth
(Continued)

FOREIGN PATENT DOCUMENTS

EP  0 748 614 A  12/1996
(Continued)

OTHER PUBLICATIONS

"What Endoscopic Accessories Do We Really Need?", C. Paul Swain, Erging Technologies in Gastrointestinal Endoscopy, Gastrointest. Endosc., vol. 7,No. 2, pp. 313-330 (Apr. 1997).
Kosmahl, Edmund; University of Scanton—Department of Physical Therapy; http://academic.uofs.edu/faculty/kosmahle1/courses/pt245/levicep.htm; 2000; pp. 1 and 1-3.

*Primary Examiner* — S. Thomas Hughes
*Assistant Examiner* — Jonathan W Miles
(74) *Attorney, Agent, or Firm* — Mayback & Hoffman P.A.; Gregory L. Mayback; Rebecca A. Tie

(57) ABSTRACT

An apparatus for the transoral invagination and fundoplication of the stomach to the esophagus includes a clip applier having sharp toothed jaws for grasping and damaging the fundus prior to applying the clip. The clip applier has an overall diameter of less than 7 mm. The clip applier jaws are coupled to a pull wire via a linkage which increases the mechanical advantage and thus permits greater grasping force. A plurality of clip designs are also provided.

32 Claims, 19 Drawing Sheets

U.S. PATENT DOCUMENTS

| | | |
|---|---|---|
| 546,416 A | 9/1895 | Copeland |
| 1,756,670 A | 4/1930 | Treat |
| 2,246,495 A | 6/1941 | Alessi et al. |
| 2,919,621 A | 1/1960 | Langdon |
| 3,618,447 A | 11/1971 | Goins |
| 3,851,359 A | 12/1974 | Wilson |
| 4,038,987 A | 8/1977 | Komiya |
| 4,044,429 A | 8/1977 | Wagner |
| 4,346,869 A | 8/1982 | MacNeill |
| 4,390,019 A | 6/1983 | LeVeen et al. |
| 4,418,694 A | 12/1983 | Beroff et al. |
| 4,430,997 A | 2/1984 | DiGiovanni et al. |
| 4,444,187 A | 4/1984 | Perlin |
| 4,454,875 A | 6/1984 | Pratt et al. |
| 4,476,865 A | 10/1984 | Failla et al. |
| 4,512,345 A | 4/1985 | Green |
| 4,562,346 A | 12/1985 | Hayashi et al. |
| 4,570,623 A | 2/1986 | Ellison et al. |
| 4,572,181 A | 2/1986 | Mattler |
| 4,719,917 A | 1/1988 | Barrows et al. |
| 4,741,336 A | 5/1988 | Failla et al. |
| 4,765,335 A | 8/1988 | Schmidt et al. |
| 4,793,335 A | 12/1988 | Frey et al. |
| 4,835,824 A | 6/1989 | Durham et al. |
| 4,844,066 A | 7/1989 | Stein |
| 4,848,328 A | 7/1989 | Laboureau |
| 4,919,152 A | 4/1990 | Ger |
| 4,960,420 A | 10/1990 | Goble |
| 4,988,355 A | 1/1991 | Leveen et al. |
| 5,002,562 A | 3/1991 | Oberlander |
| 5,022,126 A | 6/1991 | Davis |
| 5,030,226 A | 7/1991 | Green et al. |
| 5,049,153 A | 9/1991 | Nakao et al. |
| 5,099,827 A | 3/1992 | Melzer et al. |
| 5,100,420 A | 3/1992 | Green et al. |
| 5,156,609 A * | 10/1992 | Nakao et al. ............... 606/142 |
| 5,159,730 A | 11/1992 | Radvin |
| 5,163,945 A | 11/1992 | Ortiz et al. |
| 5,171,249 A | 12/1992 | Stefanchik et al. |
| 5,174,276 A | 12/1992 | Crockard |
| 5,188,636 A * | 2/1993 | Fedotov ..................... 606/144 |
| 5,207,692 A | 5/1993 | Kraus et al. |
| 5,222,961 A | 6/1993 | Nakao et al. |
| 5,269,804 A | 12/1993 | Bales et al. |
| 5,271,543 A | 12/1993 | Grant et al. |
| 5,312,426 A | 5/1994 | Segawa et al. |
| 5,312,434 A | 5/1994 | Crainich |
| 5,318,528 A | 6/1994 | Heaven et al. |
| 5,330,442 A | 7/1994 | Green et al. |
| 5,352,229 A | 10/1994 | Goble |
| 5,354,306 A | 10/1994 | Garvey, III et al. |
| 5,354,312 A | 10/1994 | Brinkerhoff et al. |
| 5,361,463 A | 11/1994 | Revis |
| 5,366,459 A | 11/1994 | Yoon |
| 5,383,880 A | 1/1995 | Hooven |
| 5,389,104 A | 2/1995 | Hahnen et al. |
| 5,395,030 A | 3/1995 | Kuramoto et al. |
| 5,395,369 A | 3/1995 | McBrayer et al. |
| 5,403,326 A | 4/1995 | Harrison et al. |
| 5,425,737 A | 6/1995 | Burbank et al. |
| 5,425,740 A | 6/1995 | Hutchinson, Jr. |
| 5,433,721 A | 7/1995 | Hooven et al. |
| 5,439,156 A | 8/1995 | Grant et al. |
| 5,439,468 A | 8/1995 | Schulze et al. |
| 5,439,479 A | 8/1995 | Shichman et al. |
| 5,441,509 A | 8/1995 | Vidal et al. |
| 5,464,416 A | 11/1995 | Steckel |
| 5,474,570 A | 12/1995 | Kockerling et al. |
| 5,482,054 A | 1/1996 | Slater et al. |
| 5,487,746 A | 1/1996 | Yu et al. |
| 5,497,933 A | 3/1996 | DeFonzo et al. |
| 5,501,693 A | 3/1996 | Gravener |
| 5,522,823 A | 6/1996 | Kuntz et al. |
| 5,562,694 A | 10/1996 | Sauer et al. |
| 5,571,116 A | 11/1996 | Bolanos et al. |
| 5,573,546 A * | 11/1996 | Nakao ...................... 606/205 |
| 5,575,802 A | 11/1996 | McQuilkin et al. |
| 5,582,617 A | 12/1996 | Klieman et al. |
| 5,601,573 A | 2/1997 | Fogelberg et al. |
| 5,620,452 A | 4/1997 | Yoon |
| 5,624,379 A | 4/1997 | Ganz et al. |
| 5,632,753 A | 5/1997 | Loeser |
| 5,657,519 A | 8/1997 | Smith |
| 5,667,517 A | 9/1997 | Hooven |
| 5,673,841 A | 10/1997 | Schulze et al. |
| 5,681,330 A | 10/1997 | Hughett et al. |
| 5,707,392 A | 1/1998 | Kortenbach |
| 5,715,604 A | 2/1998 | Lanzoni |
| 5,716,374 A | 2/1998 | Francese et al. |
| 5,722,421 A | 3/1998 | Francese et al. |
| 5,741,283 A | 4/1998 | Fahy |
| 5,766,189 A | 6/1998 | Matsuno |
| 5,769,857 A | 6/1998 | Reztzov et al. |
| 5,775,345 A | 7/1998 | Chou |
| 5,779,718 A | 7/1998 | Green et al. |
| 5,792,150 A | 8/1998 | Pratt et al. |
| 5,792,165 A | 8/1998 | Klieman et al. |
| 5,800,449 A | 9/1998 | Wales |
| 5,814,054 A | 9/1998 | Kortenbach et al. |
| 5,833,695 A | 11/1998 | Yoon |
| 5,858,018 A | 1/1999 | Shipp et al. |
| 5,865,724 A | 2/1999 | Palmer et al. |
| 5,871,488 A | 2/1999 | Tovey et al. |
| 5,891,156 A | 4/1999 | Gessner et al. |
| 5,897,507 A | 4/1999 | Kortenbach et al. |
| 5,897,562 A | 4/1999 | Bolanos et al. |
| 5,904,693 A | 5/1999 | Dicesare et al. |
| 5,906,630 A | 5/1999 | Anderhub et al. |
| 5,937,488 A | 8/1999 | Geiger |
| 5,941,439 A | 8/1999 | Kammerer et al. |
| 5,993,465 A | 11/1999 | Shipp et al. |
| 5,993,476 A | 11/1999 | Groiso |
| 6,001,110 A | 12/1999 | Adams |
| 6,013,095 A | 1/2000 | Ouchi |
| 6,015,417 A | 1/2000 | Reynolds |
| 6,059,799 A | 5/2000 | Aranyi |
| 6,083,242 A | 7/2000 | Cook |
| 6,086,600 A | 7/2000 | Kortenbach |
| 6,099,537 A | 8/2000 | Sugai et al. |
| 6,129,683 A | 10/2000 | Sutton et al. |
| 6,139,555 A | 10/2000 | Hart et al. |
| 6,149,658 A | 11/2000 | Gardiner et al. |
| 6,149,660 A | 11/2000 | Laufer et al. |
| 6,159,223 A | 12/2000 | Danks et al. |
| 6,162,233 A | 12/2000 | Williamson et al. |
| 6,238,414 B1 | 5/2001 | Griffiths |
| 6,269,819 B1 | 8/2001 | Oz et al. |
| 6,352,503 B1 | 3/2002 | Matsui et al. |
| 6,387,041 B1 | 5/2002 | Harai et al. |
| 6,425,900 B1 | 7/2002 | Knodel et al. |
| 6,517,555 B1 | 2/2003 | Caro |
| 6,551,315 B2 | 4/2003 | Kortenbach |
| 6,554,850 B1 * | 4/2003 | Ouchi et al. ............... 606/205 |
| 6,560,488 B1 | 5/2003 | Crawford |
| 6,569,085 B2 | 5/2003 | Kortenbach et al. |
| 6,578,759 B1 | 6/2003 | Ortiz |
| 6,673,092 B1 * | 1/2004 | Bacher ..................... 606/205 |
| 6,716,226 B2 | 4/2004 | Sixto, Jr. et al. |
| 6,746,450 B1 | 6/2004 | Wall et al. |
| 6,824,548 B2 | 11/2004 | Smith et al. |
| 6,843,794 B2 | 1/2005 | Sixto, Jr. et al. |
| 6,945,979 B2 | 9/2005 | Kortenbach et al. |
| 7,070,602 B2 | 7/2006 | Smith et al. |
| 7,090,685 B2 | 8/2006 | Kortenbach et al. |
| 7,232,445 B2 * | 6/2007 | Kortenbach et al. ......... 606/142 |
| 7,727,246 B2 | 6/2010 | Sixto, Jr. et al. |
| 2001/0056282 A1 | 12/2001 | Sonnenschein et al. |
| 2002/0068935 A1 | 6/2002 | Koretenbach et al. |
| 2002/0082621 A1 | 6/2002 | Schurr et al. |
| 2002/0104199 A1 | 8/2002 | Chen |
| 2002/0198537 A1 | 12/2002 | Sixto, Jr. et al. |
| 2002/0198538 A1 | 12/2002 | Kortenbach et al. |
| 2002/0198549 A1 | 12/2002 | Sixto, Jr. et al. |
| 2003/0014065 A1 | 1/2003 | Osterlind |
| 2005/0003333 A1 | 1/2005 | Zilman |
| 2005/0107809 A1 | 5/2005 | Litscher et al. |

FOREIGN PATENT DOCUMENTS

| | | |
|---|---|---|
| GB | 2 054 730 A | 2/1981 |
| JP | 2000-287981 | 10/2000 |
| JP | 2001187061 A | 7/2001 |
| JP | 2005518227 T | 6/2005 |

* cited by examiner

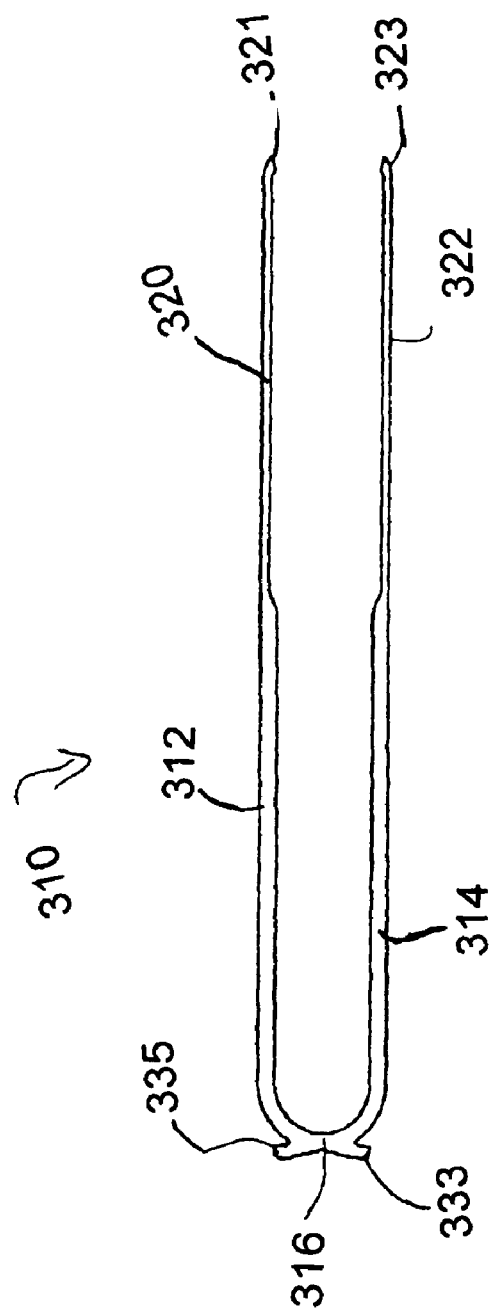
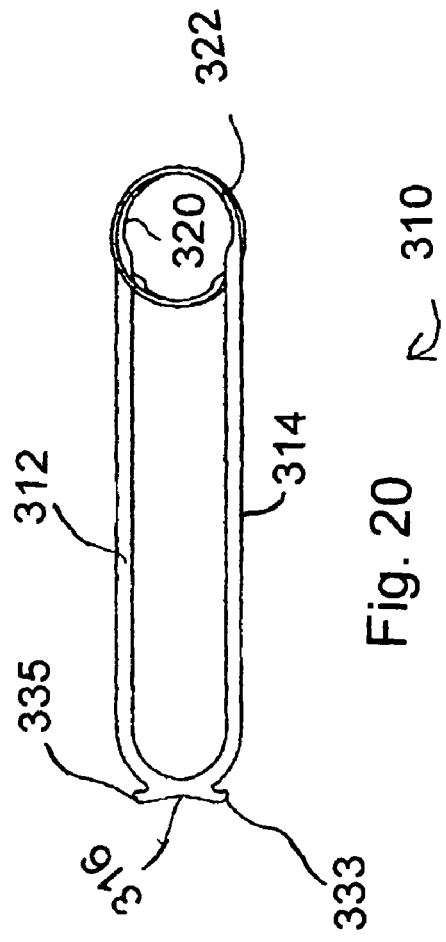

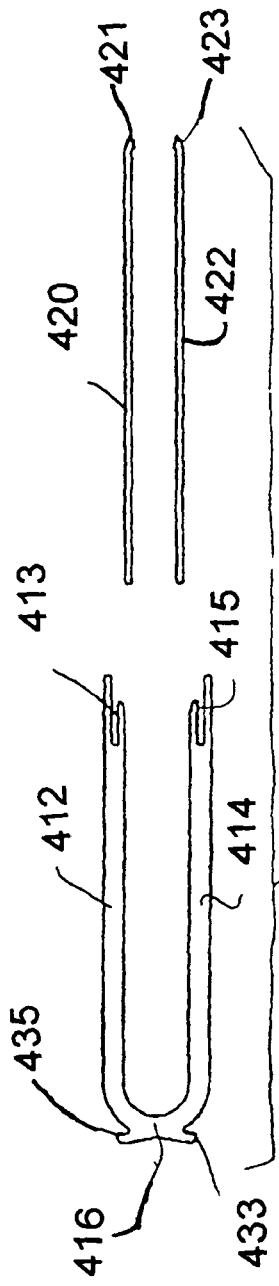
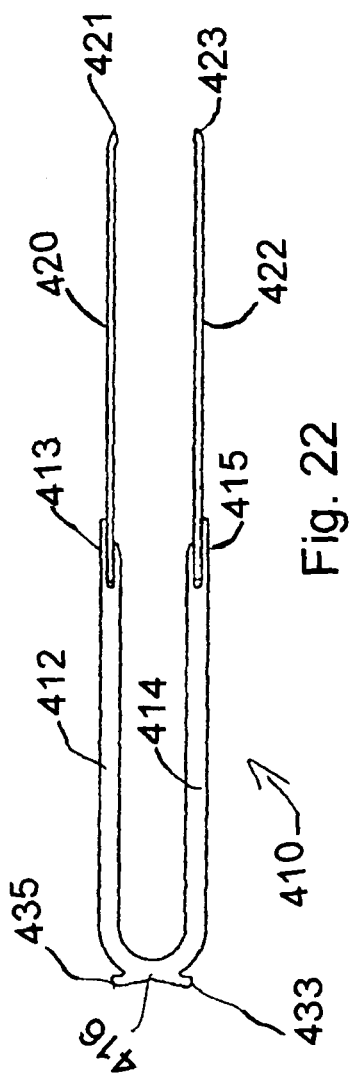
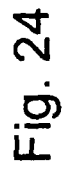
Fig. 21
Fig. 22
Fig. 23
Fig. 24

SURGICAL CLIP APPLICATION ASSEMBLY

CROSS-REFERENCE TO RELATED APPLICATIONS

This application is a divisional application of co-owned application Ser. No. 10/010,247 filed Dec. 6, 2001, now U.S. Pat. No. 7,232,445 which claims the benefit of provisional application Ser. No. 60/292,419, filed May 21, 2001, is related to co-owned application Ser. Nos. 10/010,908, 10/010,244, and 10/010,246, all three filed on Dec. 6, 2001, Ser. No. 11/726,248 filed on Mar. 21, 2007, 11/728,502 filed on Mar. 26, 2007, and is a continuation-in-part of application Ser. No. 09/931,528, filed Aug. 16, 2001,now U.S. Pat. No. 6,569,085 Ser. No. 09/891,775, filed Jun. 25, 2001, now U.S. Pat. No. 6,716,226 and Ser. No. 09/730,911, filed Dec. 6, 2000, now U.S. Pat. No. 6,551,315 the complete disclosures of which are hereby incorporated by reference herein in their entireties.

BACKGROUND OF THE INVENTION

1. Field of the Invention

The invention relates to endoscopic surgical instruments. More particularly, the invention relates to flexible instruments for the transoral invagination and fundoplication of the stomach to the esophagus.

2. State of the Art

Gastroesophageal fundoplication is a procedure for the treatment of gastroesophageal reflux disease (GERD), a condition in which gastric acids are regurgitated into the esophagus resulting in one or more of esophagitis, intractable vomiting, asthma, and aspiration pneumonia. The fundoplication procedure involves wrapping the fundus of the stomach around the lower end of the esophagus and fastening it in place. Traditionally, this procedure is accomplished via open surgery with the use of sutures to secure the plicated fundus of the stomach around the esophagus without penetrating (incising) the stomach. Although traditional fundoplication involves plicating the fundus and the esophagus, as used herein the term includes plicating the fundus to itself near the esophagus.

U.S. Pat. No. 5,403,326 to Harrison et al. discloses a method of performing endoscopic fundoplication using surgical staples or two-part surgical fasteners. The procedure disclosed by Harrison et al. involves performing two percutaneous endoscopic gastrotomies (incisions through the skin into the stomach) and the installation of two ports through which a stapler, an endoscope, and an esophageal manipulator (invagination device) are inserted. Under view of the endoscope, the esophageal manipulator is used to pull the interior of the esophagus into the stomach. When the esophagus is in position, with the fundus of the stomach plicated, the stapler is moved into position around the lower end of the esophagus and the plicated fundus is stapled to the esophagus. The process is repeated at different axial and rotary positions until the desired fundoplication is achieved. While, the procedure disclosed by Harrison et al. is a vast improvement over open surgery, it is still relatively invasive requiring two incisions through the stomach.

U.S. Pat. No. 5,571,116 to Bolanos et al. discloses a non-invasive treatment of gastroesophageal reflux disease which utilizes a remotely operable invagination device and a remotely operable surgical stapler, both of which are inserted transorally through the esophagus. According to the methods disclosed by Bolanos et al., the invagination device is inserted first and is used to clamp the gastroesophageal junction. The device is then moved distally, pulling the clamped gastroesophageal junction into the stomach, thereby invaginating the junction and involuting the surrounding fundic wall. The stapler is then inserted transorally and delivered to the invaginated junction where it is used to staple the fundic wall.

Bolanos et al. disclose several different invagination devices and several different staplers. Generally, each of the staplers disclosed by Bolanos et al. has an elongate body and a spring biased anvil which is rotatable approximately 15 degrees away from the body in order to locate the invaginated gastroesophageal junction between the body and the anvil. The body contains a staple cartridge holding a plurality of staples, and a staple firing knife. Each of the invagination devices disclosed by Bolanos et al. has a jaw member which is rotatable at least 45 degrees and in some cases more than 90 degrees to an open position for grasping the gastroesophageal junction. One of the chief disadvantages of the methods and apparatus disclosed by Bolanos et al. is that the stapler and the invagination device must both be present in the esophagus at the same time. With some of the embodiments disclosed, the presence of both instruments is significantly challenged by the size of the esophagus. In addition, the actuating mechanism of the device disclosed by Bolanos et al. is awkward. In particular, the stapler anvil is biased to the open position, and it is not clear whether or not the stapler anvil can be locked in a closed position without continuously holding down a lever. In addition, it appears that the staple firing trigger can be inadvertently operated before the anvil is in the closed position. This would result in inadvertent ejection of staples into the stomach or the esophagus of the patient.

U.S. Pat. No. 6,086,600 to Kortenbach discloses an endoscopic surgical instrument including a flexible tube, a grasping and fastening end effector coupled to the distal end of the tube, and a manual actuator coupled to the proximal end of the tube. The manual actuator is coupled to the end effector by a plurality of flexible cables which extend through the tube. The tube contains a lumen for receiving a manipulable endoscope and the end effector includes a passage for the distal end of the endoscope. The end effector has a store for a plurality of male fastener parts, a store for a plurality of female fastener parts, a rotatable grasper, a rotatable fastener head for aligning a female fastener part and a male fastener part with tissues therebetween, and a firing member for pressing a male fastener part through tissues grasped by the grasper and into a female fastener part. According to a stated preferred embodiment, the overall diameters of the flexible tube and the end effector (when rotated to the open position) do not exceed approximately 20 mm so that the instrument may be delivered transorally to the fundus of the stomach.

While transoral invagination and fundoplication apparatus and procedures have improved over the years, it is still difficult to deliver and manipulate the necessary apparatus transorally. The primary reason for the difficulty is that the overall diameter, or more accurately the cross sectional area, of the equipment is too large. Notwithstanding Kortenbach's reference to 20 mm, most of the equipment in use today is at least 24 mm in diameter. Moreover, even if the equipment could be reduced to 20 mm in diameter (314 mm$^2$ cross sectional area), it would still be difficult to manipulate. Those skilled in the art will appreciate that larger instruments are less pliable and that the invagination and fundoplication procedure requires that the instruments turn nearly 180 degrees. Moreover, it will be appreciated that large instruments obscure the endoscopic view of the surgical site.

Still other issues which need to be addressed in this procedure include the need to suitably grasp the fundus before plication so that all layers of the fundus are plicated. Preferably, plication damages the fundus so that adhesion occurs during healing.

3. Co-Owned Technology

Previously incorporated application Ser. No. 09/730,911, filed Dec. 6, 2000, entitled "Methods and Apparatus for the Treatment of Gastric Ulcers", discloses a surgical tool which is delivered to a surgical site over an endoscope rather than through the working lumen of an endoscope.

Co-owned provisional application Ser. No. 60/292,419, filed May 21, 2001, entitled "Methods and Apparatus for On-Endoscope Instruments Having End Effectors and Combinations of On-Endoscope and Through-Endoscope Instruments", discloses many tools and procedures including an on-scope grasper assembly having grasping jaws, and a through-scope clip applier having jaws adapted to close about tissue and apply a clip over and/or through the tissue. In operation, the grasper jaws may grab and hold tissue, e.g., the fundus of the stomach or esophageal tissue, while the jaws of the clip applier surround a portion of the tissue held by the grasper jaws and apply a clip thereover.

Previously incorporated application Ser. No. 09/891,775, filed Jun. 25, 2001, entitled "Surgical Clip", discloses a surgical clip having a U-shaped configuration with first and second arms, and a bridge portion therebetween. The first arm is provided with a tip preferably having a catch, and the second arm extends into a deformable retainer having a tissue-piercing end and preferably also a hook. During application, tissue is clamped, and the clip is forced over the clamped tissue and the retainer of the second arm is bent and may be pierced through the tissue. The retainer is toward and around or adjacent the tip of the first arm preferably until the hook is engaged about the catch to secure the clip to the tissue and prevent the clip and tissue from separating. The clip is provided with structure that facilitates the stacking of a plurality of clips in a clip chamber of a clip applier.

Previously incorporated application Ser. No. 09/931,528, filed Aug. 16, 2001, entitled "Methods and Apparatus for Delivering a Medical Instrument Over an Endoscope while the Endoscope is in a Body Lumen", discloses methods and apparatus for delivering a medical instrument over the exterior of an endoscope while the endoscope is installed in the patient's body in order to allow the use of instruments which are too large to fit through the lumina of an endoscope.

The previously incorporated simultaneously filed application entitled "Flexible Surgical Clip Applier", discloses a surgical clip applier having a pair of clip applying jaws at the distal end of an outer coil, a set of pull wires extending through the outer coil and coupled to the jaws, and a push wire extending through the outer coil. A clip chamber is provided in the distal end of the coil. A clip pusher is provided at a distal end of the push wire, and adapted to advance a clip into the jaws. The jaws include clamping surfaces which operate to compress tissue between the jaws when the jaws are closed, channels in which a distalmost clip rides when the jaws are closed and the pusher is advanced thereby causing the distalmost clip to be pushed over the tissue, and distal anvil portions which operate to bend a portion of the distalmost clip to facilitate its retention on the clamped tissue. The clip applier is capable of providing a pushing force far in excess of a perceived possible maximum of the 200 grams (0.44 lbs) published in the art. One embodiment of the device of the invention provides a pushing force in excess of 2267 grams (5 lbs).

SUMMARY OF THE INVENTION

It is therefore an object of the invention to provide methods and apparatus for transoral invagination and fundoplication.

It is also an object of the invention to provide an apparatus for transoral invagination and fundoplication which is easy to manipulate.

It is another object of the invention to provide an apparatus for transoral invagination and fundoplication which has a relatively small cross-sectional area.

It is still another object of the invention to provide methods and apparatus for fundoplication which combine the relative advantages of staples and two-part fasteners, i.e. the small size of a staple and the greater integrity of a two-part fastener.

It is yet another object of the invention to provide methods and apparatus for transoral invagination and fundoplication which damages tissue such that adhesion occurs during healing.

In accord with these objects which will be discussed in detail below, the methods of the invention include delivering a grasper, a clip applier, and an endoscope transorally to the site of fundoplication; grasping the fundus with the grasper (or similar device, e.g. corkscrew) and pulling it into the jaws of the clip applier; closing the jaws of the clip applier over the fundus and applying a clip to the fundus. The method is repeated at different locations until the desired fundoplication is achieved. The apparatus of the invention includes a clip applier having sharp toothed jaws for grasping and damaging the fundus prior to applying the clip. The clip applier has an overall diameter of less than 7 mm and may be delivered through a 7 mm sleeve which attaches to a 12 mm endoscope having a lumen through which the grasper is delivered. The overall cross-sectional area of the apparatus is therefore approximately 152 $mm^2$ as compared to the 314 $mm^2$ of the prior art devices. Alternatively, the clip applier and the grasper may be delivered through an endoscope having two 6 mm lumina.

According to a presently preferred embodiment, the clip applier jaws are coupled to a pull wire via a linkage which increases the mechanical advantage and thus permits greater grasping force.

A plurality of clip designs are provided. Some embodiments include a pair of arms coupled by a bridge and a single locking retainer. Other embodiments include dual parallel coiled retainers. According to one embodiment, the clip has two detachable retainers which are installed in the fundus and the clip arms and bridge are removed.

Additional objects and advantages of the invention will become apparent to those skilled in the art upon reference to the detailed description taken in conjunction with the provided figures.

BRIEF DESCRIPTION OF THE DRAWINGS

FIG. 19 is a side elevational view of a second embodiment of a clip according to the invention prior to application;

FIG. 20 is a side elevational view of the clip of FIG. 19 after application;

FIG. 21 is a side elevational view of a third embodiment of a clip according to the invention prior to assembly;

FIG. 22 is a side elevational view of the clip of FIG. 21 assembled prior to application;

FIG. 23 is a side elevational view of the applied portion of the clip of FIGS. 17 and 18;

FIG. 24 is a view similar to FIG. 23 of an alternate third embodiment of the applied portion of a clip according to the invention.

DETAILED DESCRIPTION OF EXEMPLARY EMBODIMENTS

Figure 1:
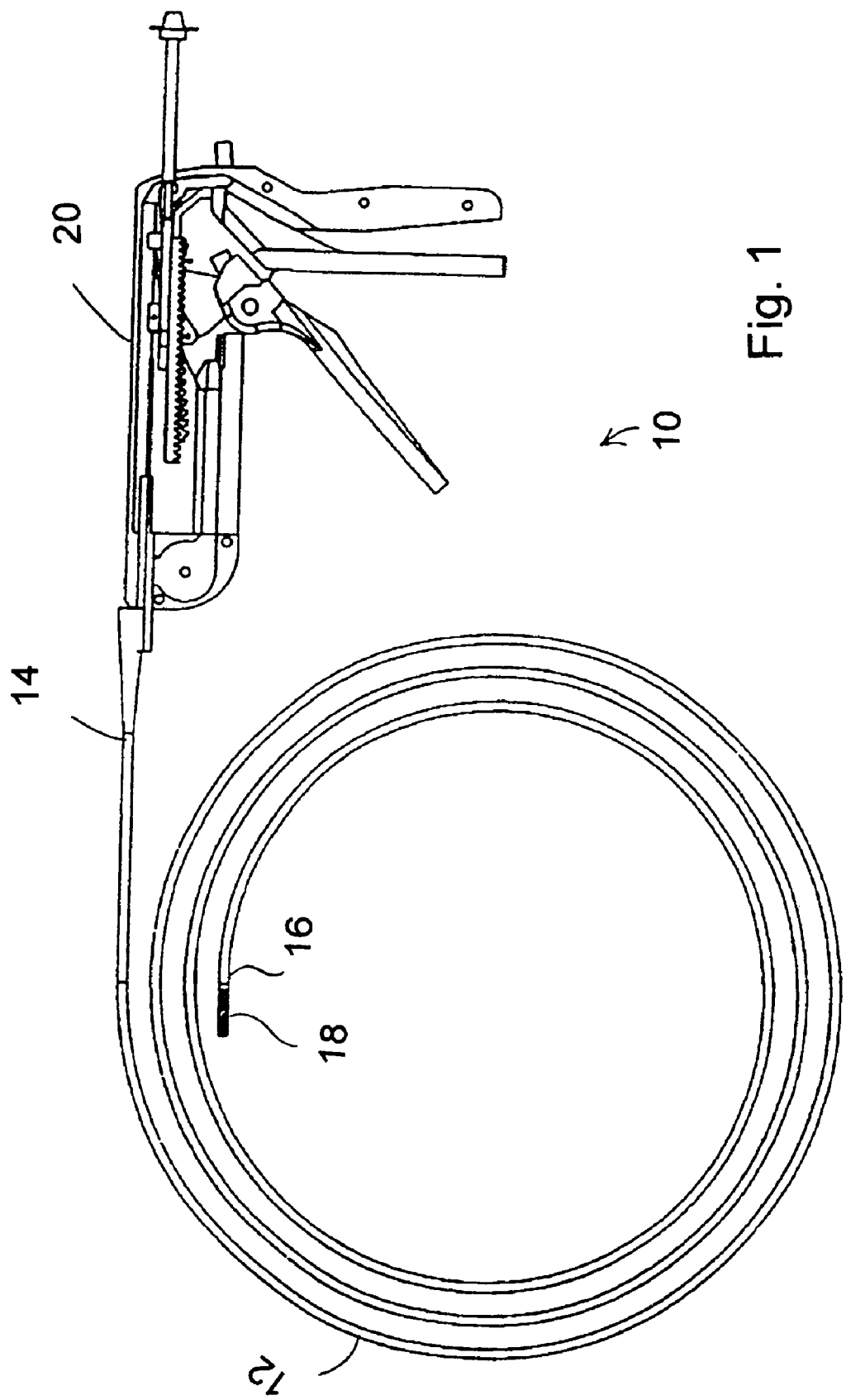
FIG. 1 is a side elevational view of a clip applier according to the invention.

Referring now to FIG. 1, a clip applier 10 according to the invention generally includes a flexible wound outer coil 12 having a proximal end 14 and a distal end 16. An end effector assembly 18 is coupled to the distal end 16 of the coil 12 and an actuator assembly 20 is coupled to the proximal end 14 of the coil 12. A plurality of pull/push wires 58, 60 (shown and described below with reference to FIGS. 2-4) extend through the coil 12 and couple the end effector assembly 18 to the actuator assembly 20. The clip applier 10 is similar to the clip applier described in detail in previously incorporated co-owned application Ser. No. 10/010,908, entitled "Flexible Surgical Clip Applier", filed simultaneously herewith. However, in this application, the end effector assembly 18 is designed specifically for fundoplication using a clip significantly larger than that used in the clip applier of the aforesaid co-owned application.

Figure 2:
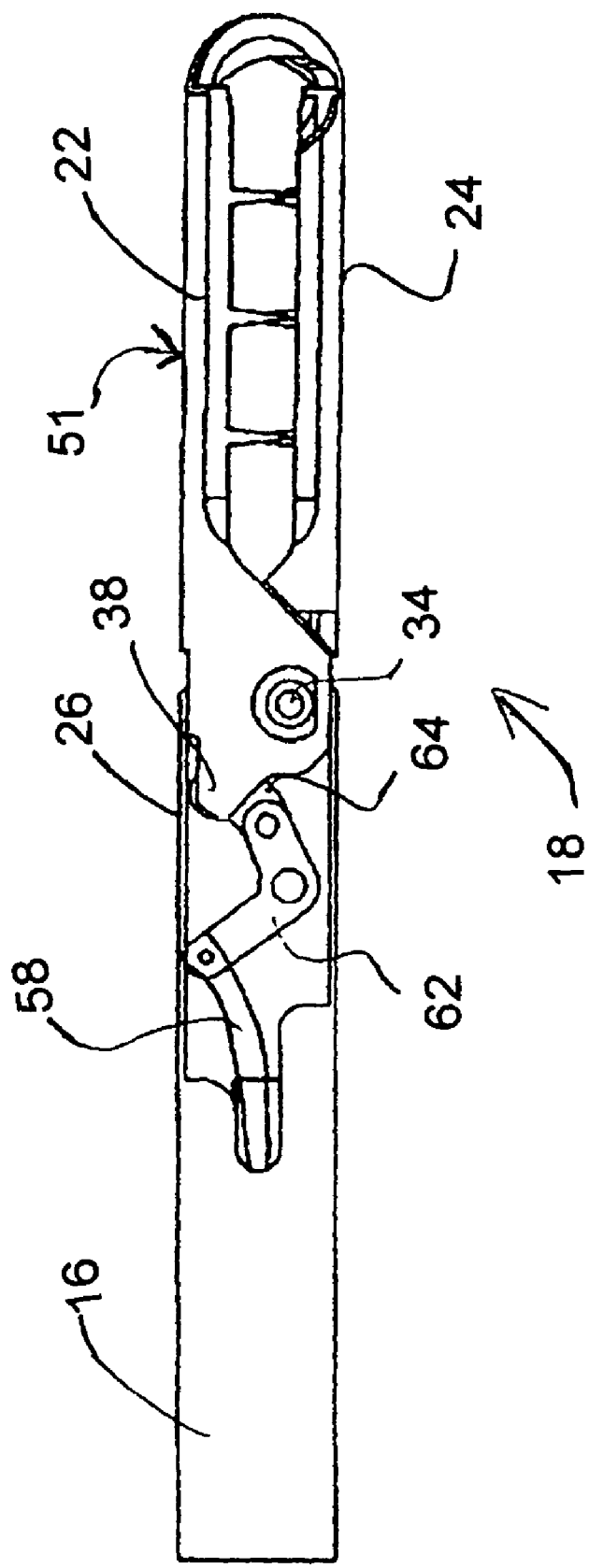
FIG. 2 is a side elevational view of a first embodiment of the distal end of the clip applier with the jaws in the closed position.
Figure 3:
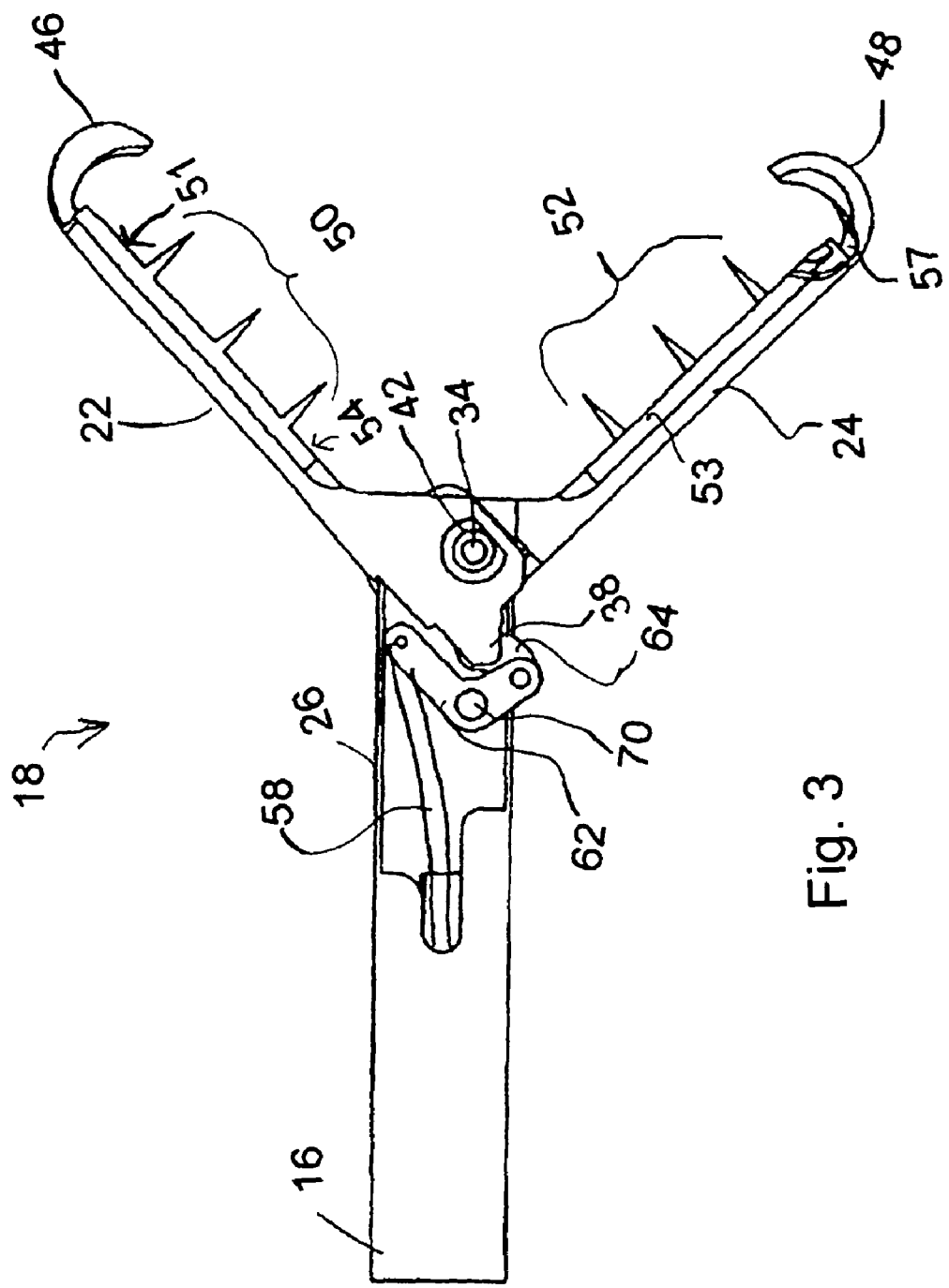
FIG. 3 is a side elevational view of a first embodiment of the distal end of the clip applier with the jaws in the open position.
Figure 4:
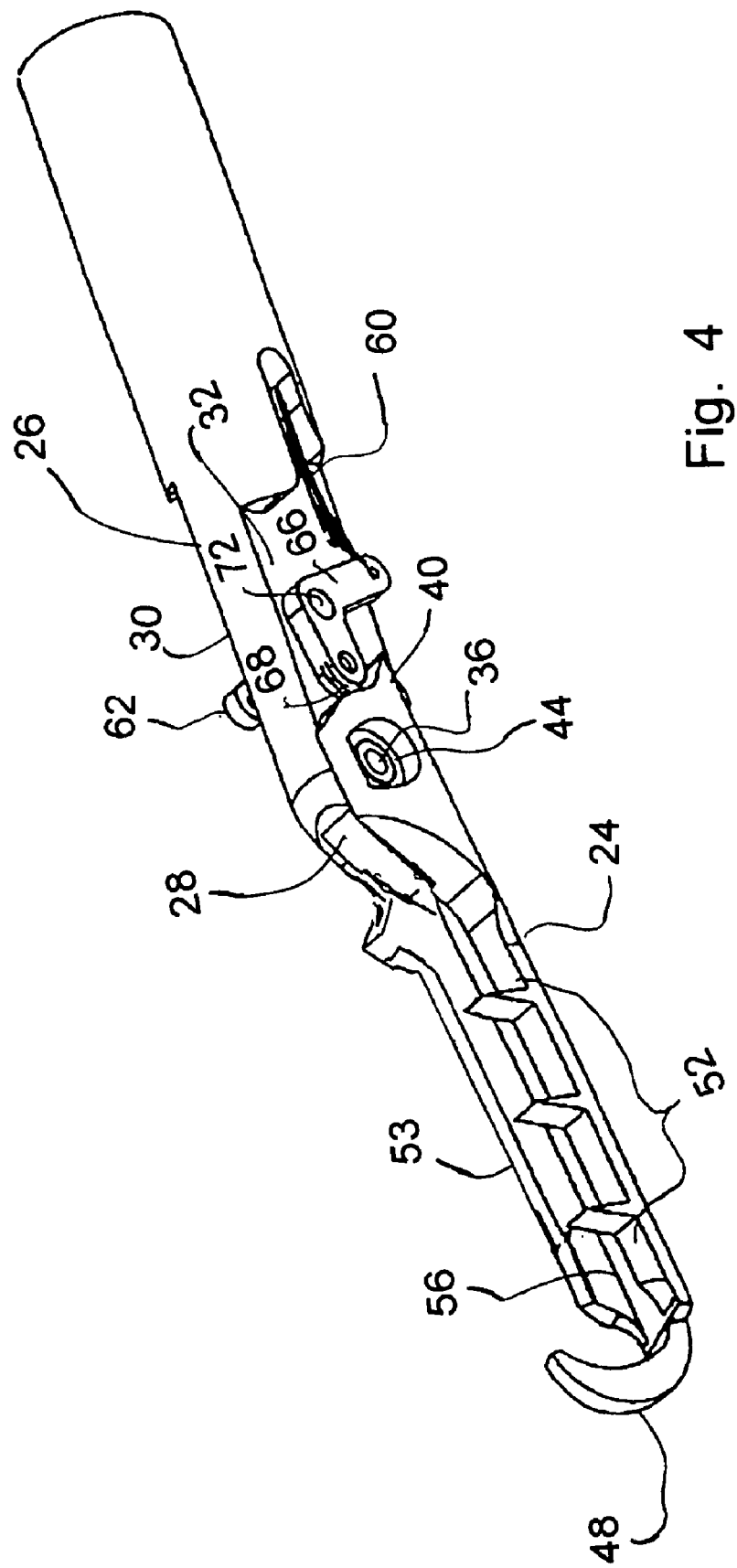
FIG. 4 is a broken isometric view of a first embodiment of the distal end of the clip applier with one jaw removed.

FIGS. 2-4 illustrate the details of the end effector assembly 18 according to a first embodiment of the invention. The end effector assembly 18 includes a pair of jaws 22, 24 which are rotatably coupled to a clevis 26. In particular, the clevis 26 has a central channel 28 (seen best in FIG. 4) which is defined by clevis arms 30, 32. Although the term "clevis" is used because of its general acceptance in the art of endoscopic instruments, the "clevis" 26 is preferably covered on top and bottom so that the only exit from the channel 28 is at the distal end. The jaw 22 is rotatably coupled to the clevis arm 30 by an axle 34 and the jaw 24 is rotatably coupled to the clevis arm 32 by an axle 36. The axles 34 and 36 are dimensioned such that they do not significantly obscure the channel 28.

The jaws 22, 24 are substantially identical. Each jaw 22, 24 includes a proximal tang 38, 40, a mounting bore 42, 44, a distal hook shaped anvil 46, 48 and a plurality of medial teeth 50, 52. As seen best in FIG. 4, the medial teeth 50, 52 are arranged on one side of the jaw and a short wall 51, 53 is arranged on the opposite side of the jaw to define a groove (or guiding channel) 54, 56. The grooves 54, 56 meet the anvils 46, 48 each of which has a helical surface. The interior (proximal) helical surfaces of the anvils act to bend the clip retainers as described below with reference to FIGS. 19-24.

The proximal tang 38, 40 of each jaw is coupled to a respective pull/push wire 58, 60 via two links 62, 64 and 66, 68. The links 62, 66 are substantially L-shaped and are rotatably coupled near their elbow to the clevis arms 30, 32 by axles 70, 72 which do not significantly obscure the channel 28 between the clevis arms. One end of the link 62, 66 is coupled to the pull/push wire 58, 60 and the other end of the link 62, 66 is rotatably coupled to one end of the link 64, 68. The other end of the link 64, 68 is rotatably coupled to the tang 38, 40. The combined coupling of each jaw 22, 24 to each pull/push wire 58, 60 forms a linkage which amplifies the force from the pull/push wires to the jaws. In particular, as the jaws close, the mechanical advantage increases.

The proximal ends of the pull/push wires 58, 60 are coupled to the actuator assembly (20 in FIG. 1) as described in previously incorporated co-owned application Ser. No. 10/010,908, entitled "Flexible Surgical Clip Applier", filed simultaneously herewith.

A clip pusher (not shown) disposed in the interior of the coil is coupled to a push wire (not shown) which is coupled to the actuator assembly as described in previously incorporated co-owned application Ser. No. 10/010,908, entitled "Flexible Surgical Clip Applier", filed simultaneously herewith. Unlike the previously incorporated co-owned application, the jaws of the instant clip applier are significantly longer and designed for use with clips approximately 17-20 mm long (after the clip is applied) as compared to the 5-7 mm clips shown in the previously incorporated co-owned application.

Figure 5:
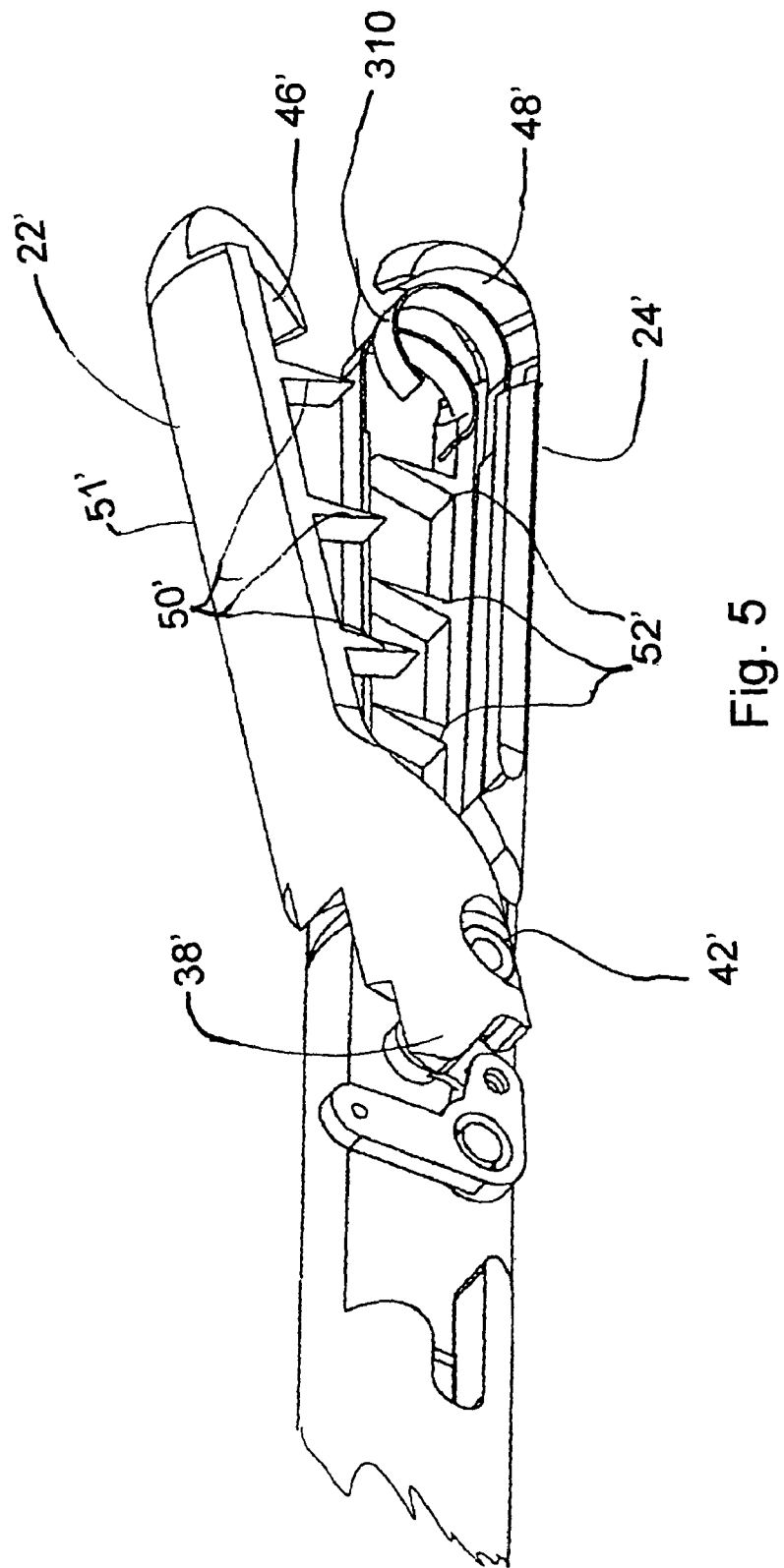
FIG. 5 is a broken isometric view of a second embodiment of the distal end of the clip applier with a clip of the type shown in FIGS. 19 and 20.
Figure 6:
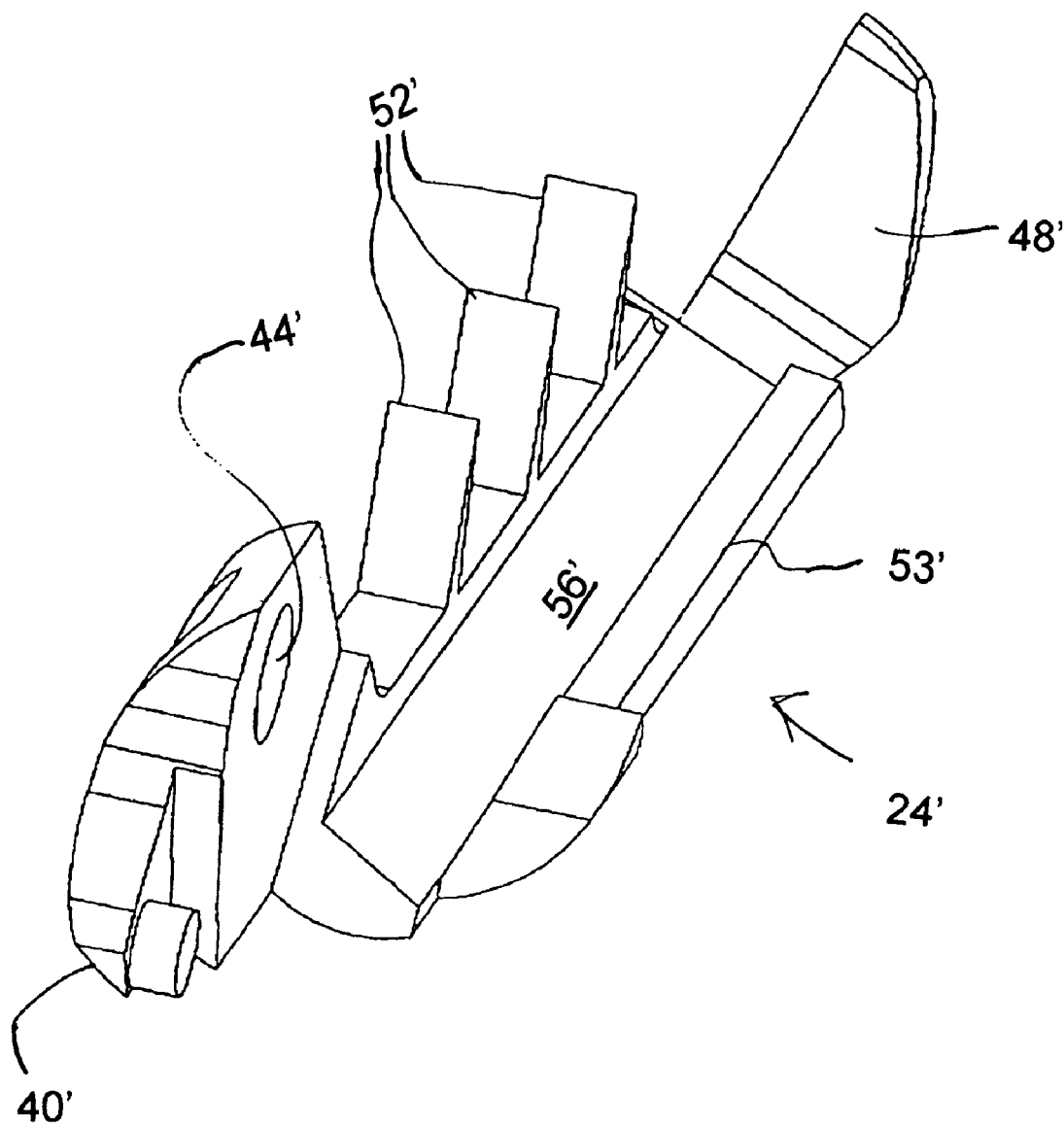
FIG. 6 is an isometric view of a single jaw of the second embodiment of the distal end of the clip applier.
Figure 7:
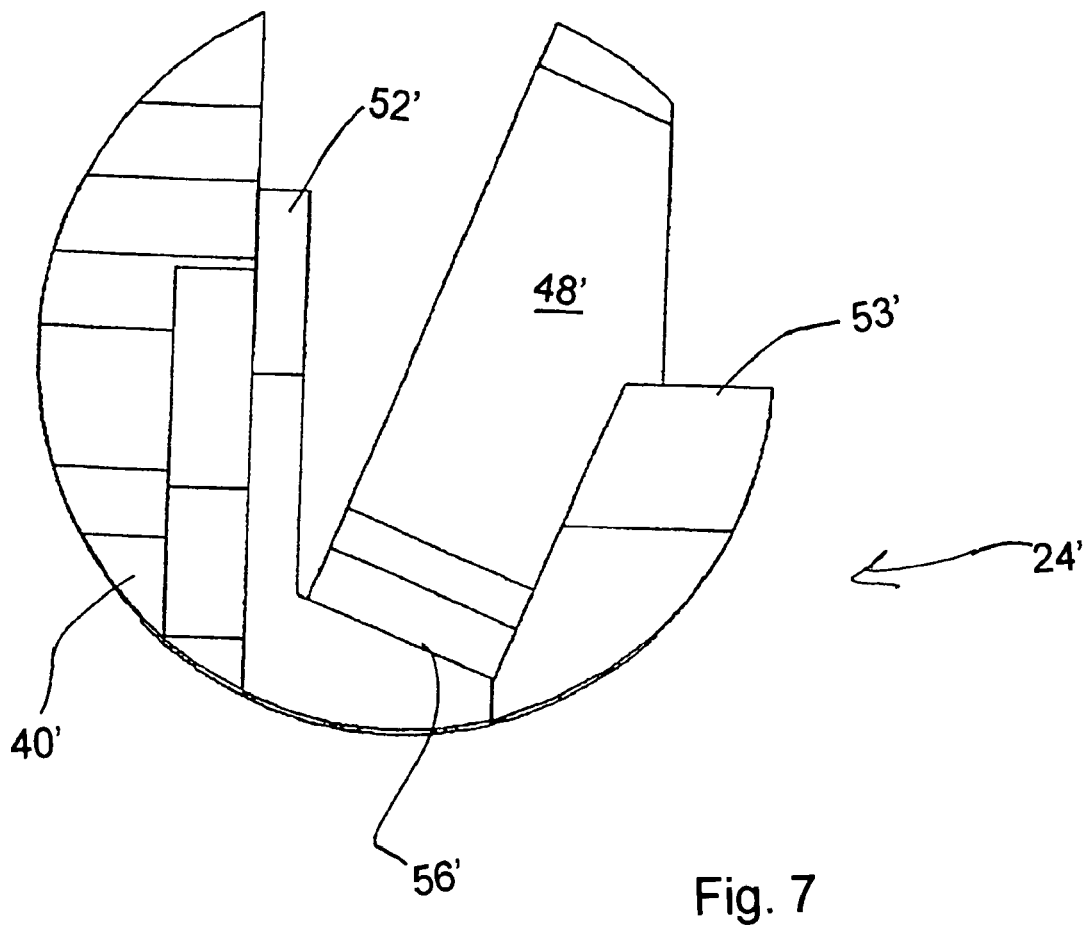
FIG. 7 is a proximal end view of the jaw of FIG. 6.
Figure 8:
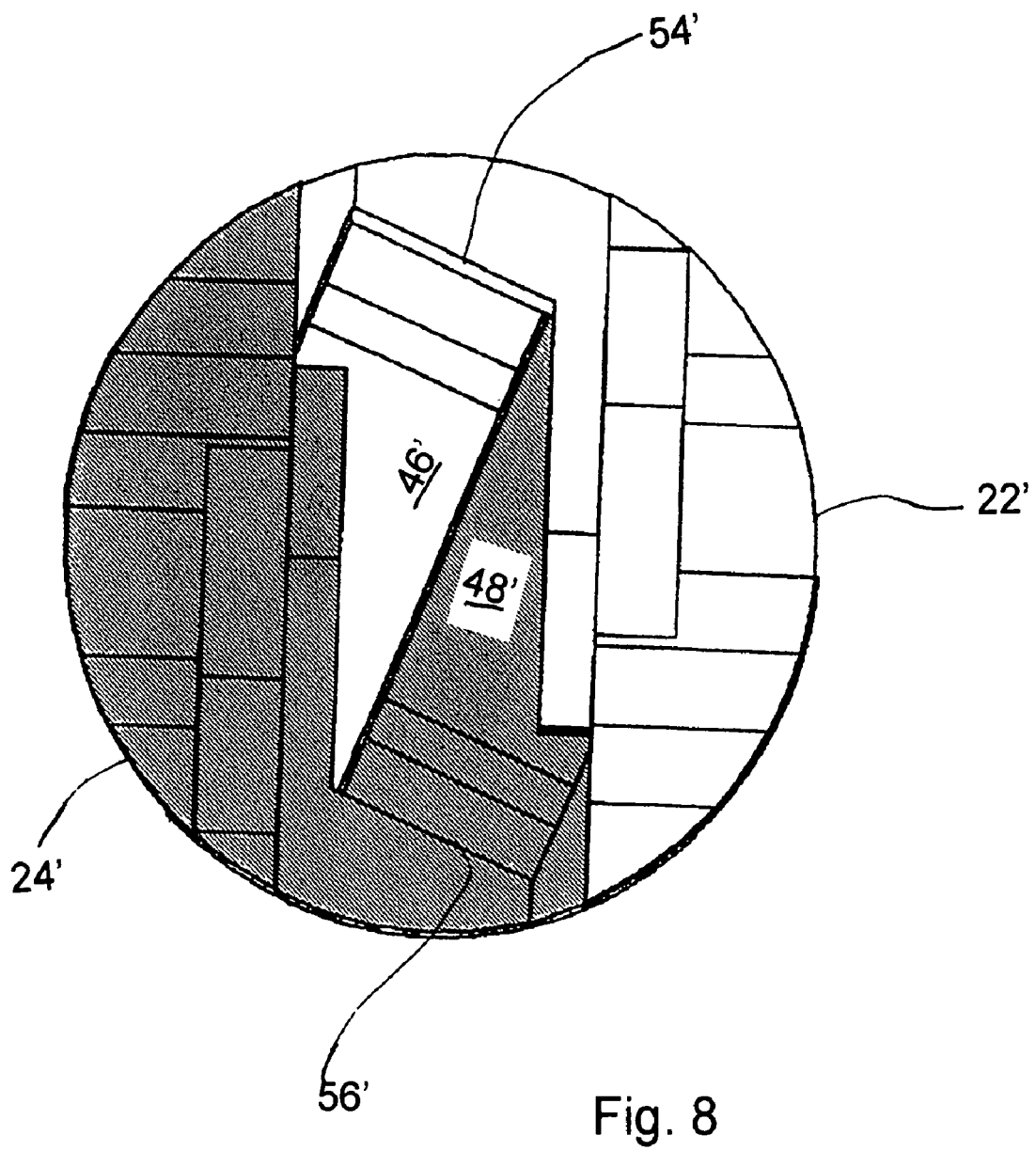
FIG. 8 is a proximal end view of the two jaws of a second embodiment of the distal end of the clip applier in the closed position with the lower jaw shaded for clarity.

Turning now to FIGS. 5-8, a second embodiment of the jaws 22', 24' is illustrated. The jaws 22', 24' are substantially identical to each other and are designed for use with any of the clips illustrated in FIGS. 19-24. Each jaw 22', 24' includes a proximal tang 38', 40', a mounting bore 42', 44', a distal hook shaped anvil 46', 48' and a plurality of medial teeth 50', 52'. The medial teeth 50', 52' are arranged on one side of the jaw and a short wall 51', 53' is arranged on the opposite side of the jaw to define a groove (or guiding channel) 54', 56'. The grooves 54', 56' meet the interior surfaces of the anvils 46', 48' which curve about a single axis. The interior surfaces of the anvils act to bend the clip retainers as described below with reference to FIGS. 19-24 and as shown by the clip 310 in FIG. 5. According to this embodiment, as seen best in FIGS. 6-8, the guiding channels 54', 56' and the anvils 46', 48' are angled relative to the vertical axis of the jaw 22', 24'. This angle causes the clip to twist as it is pushed through the jaws so that the ends of the clip are offset as shown in FIG. 5, for example. According to the presently preferred embodiment, the guiding channels 54', 56' and the anvils 46', 48' are angled approximately 22° relative to the vertical axis of the jaw 22', 24'. According to a method of the invention, clips for use with this embodiment of the jaws are pre-bent in the bridge area to facilitate movement through the angled channels.

Figure 9:
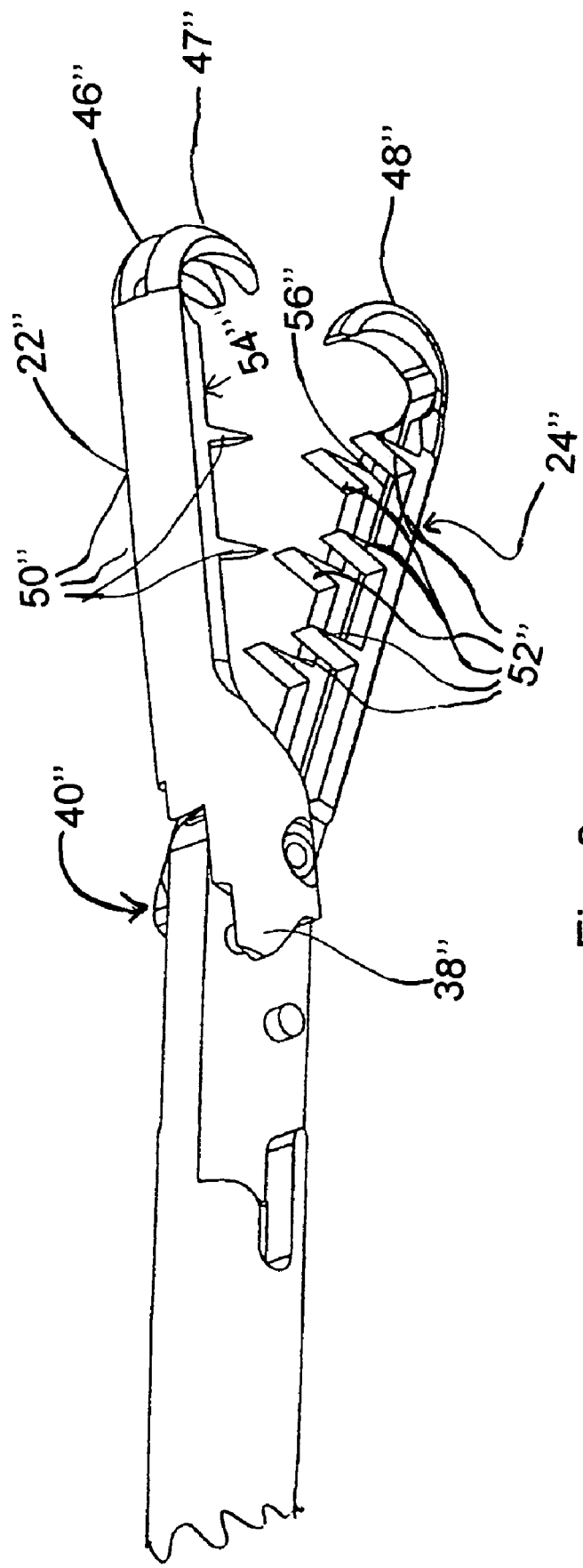
FIG. 9 is a broken isometric view of a third embodiment of the distal end of the clip applier suitable for use with a clip of the type shown in FIGS. 17 and 18 or 24.

Referring now to FIG. 9, a third embodiment of the jaws 22", 24" is illustrated. The jaws 22", 24" are not identical to each other and are designed for use with clips of the type illustrated in FIGS. 17-18. Each jaw 22", 24" includes a proximal tang 38", 40" and a mounting bore 42", 44". One jaw 22" terminates with two spaced apart distal hooks 46", 47" and has two rows of medial teeth 50". The other jaw 24" terminates with a single distal hook shaped anvil 48" and has two rows of medial teeth 52". The medial teeth 50", 52" are arranged on both sides of the jaw and a groove (or guiding channel) 54", 56" lies between the rows of teeth. The groove 54" terminates with an undercut well (not shown) as described in co-owned Ser. No. 10/010,908, whereas the groove 56" continues on to the interior of the anvil 48" which has a surface which curves about a single axis. Those skilled in the art will appreciate that when the jaws are closed, the anvil 48" will reside between the hooks 46" and 47" and the teeth 50" will be interleaved with the teeth 52". The interior surface of the anvil 48" bends the clip retainer as described below with reference to FIGS. 17-18 and as shown and described in previously incorporated co-owned application Ser. No. 09/891,775, and Ser. No. 10/010,908.

Turning now to FIGS. 10-14, a method of using the clip applier of the invention is illustrated in context with an existing endoscope 100 having a single lumen through which a small grasper 102 is supplied and an external working channel 104 which is attached to the scope 100 and through which the clip applier is delivered. The external working channel 104 is preferably one of the type described in previously incorporated application Ser. No. 09/931,528, filed Aug. 16, 2001, entitled "Methods and Apparatus for Delivering a Medical Instrument Over an Endoscope while the Endoscope is in a Body Lumen".

Figure 10:
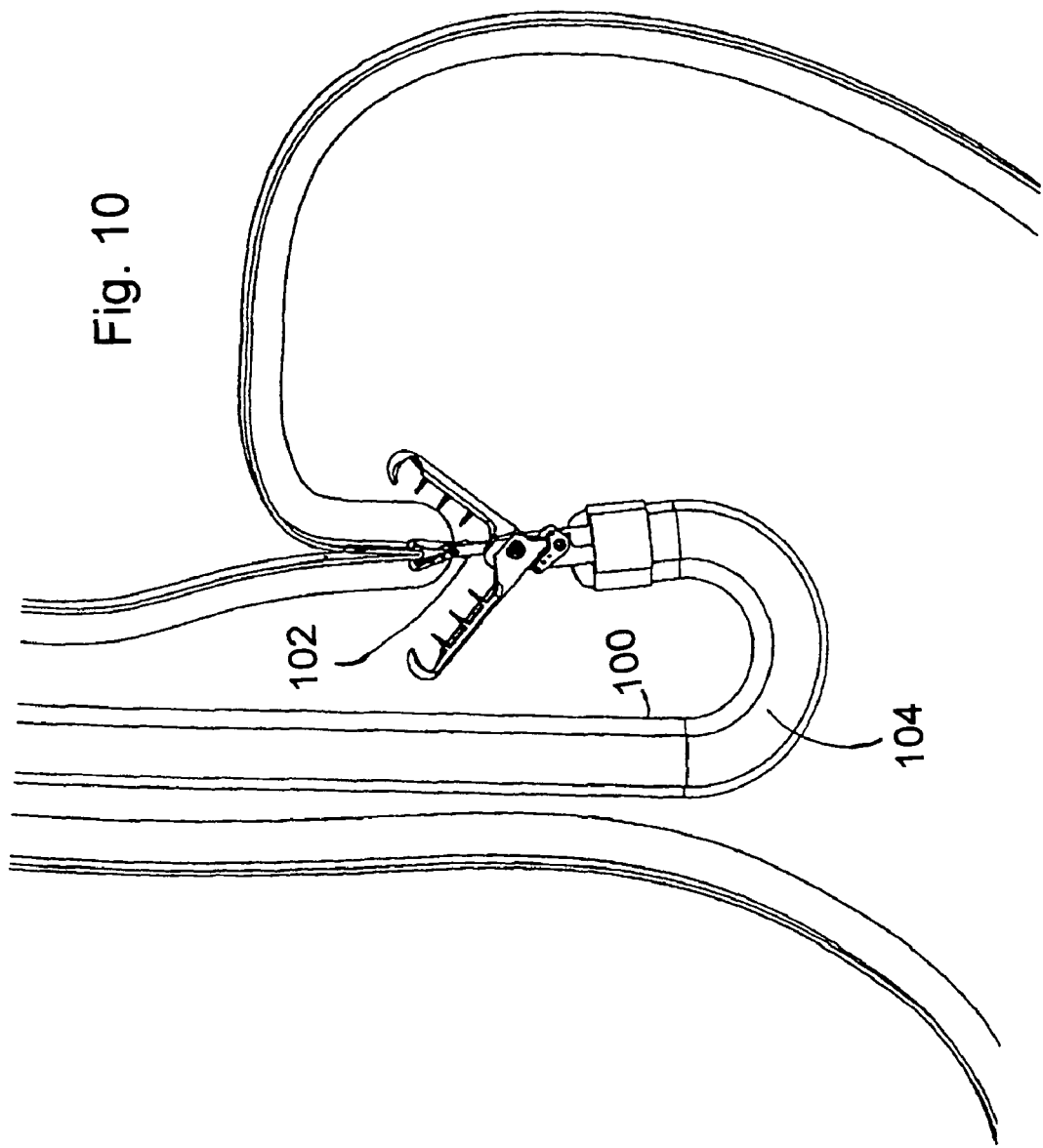
FIGS. 10-14 are schematic views illustrating a method according to the invention.
Figure 11:
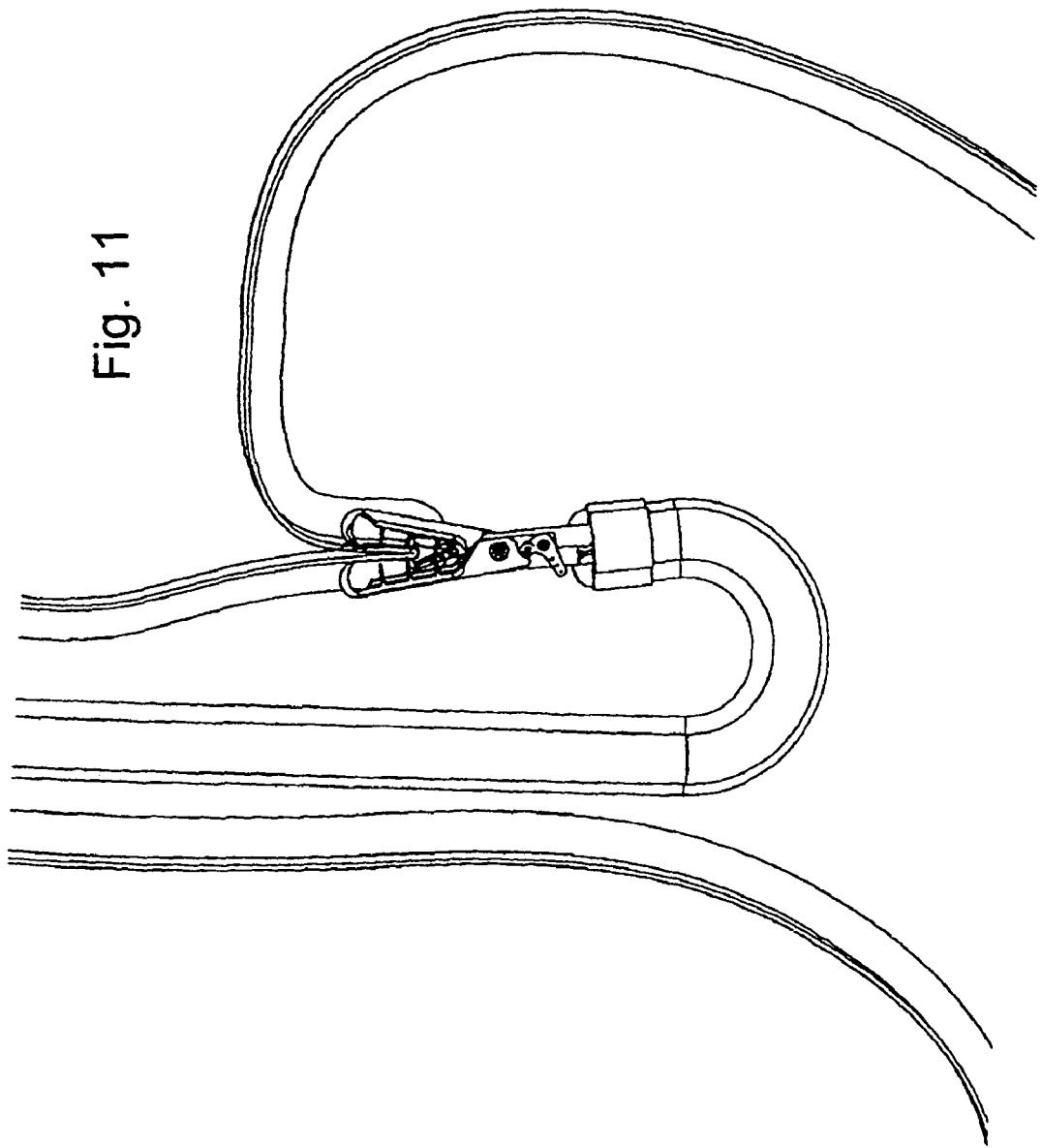
Figure 12:
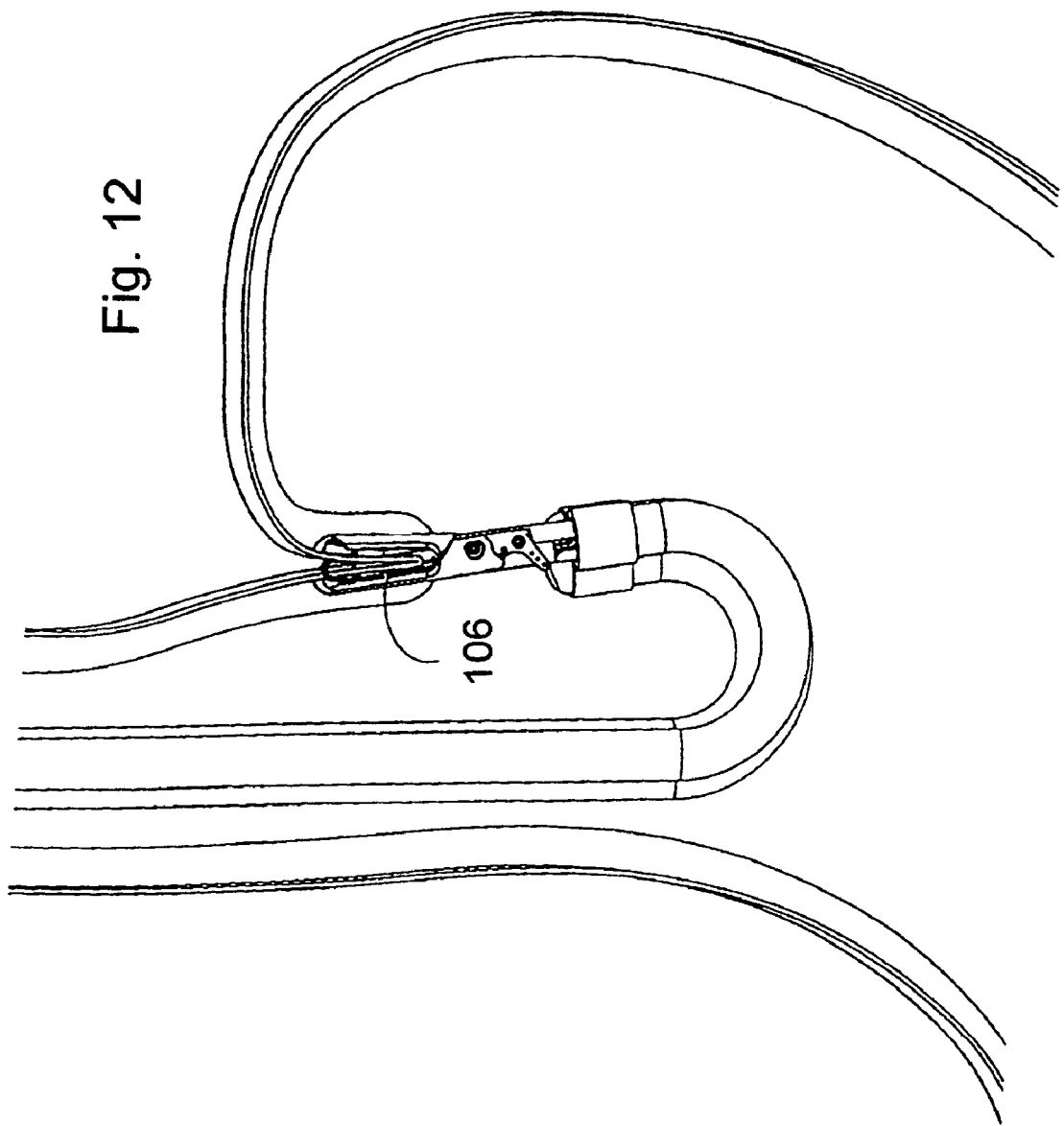

According to a method of the invention, after the endoscope assembly is delivered transorally to the procedural site, as shown in FIG. 10, the fundus is grasped by the graspers and pulled in between the open jaws of the clip applier. The jaws of the clip applier are then closed onto the invaginated fundus as shown in FIG. 11. As the jaws are closed the medial teeth of the jaws puncture the invaginated fundus as shown in FIGS. 11 and 12. When the jaws are completely closed (or closed as much as possible), they are preferably locked, the grasper is optionally released, and the clip pusher is activated to push forward, advance, and/or slide, with or without tissue contact, a clip 106 as shown in FIG. 12 and as described in the previously incorporated, co-owned, simultaneously filed application and discussed in detail hereinafter.

Figure 13:
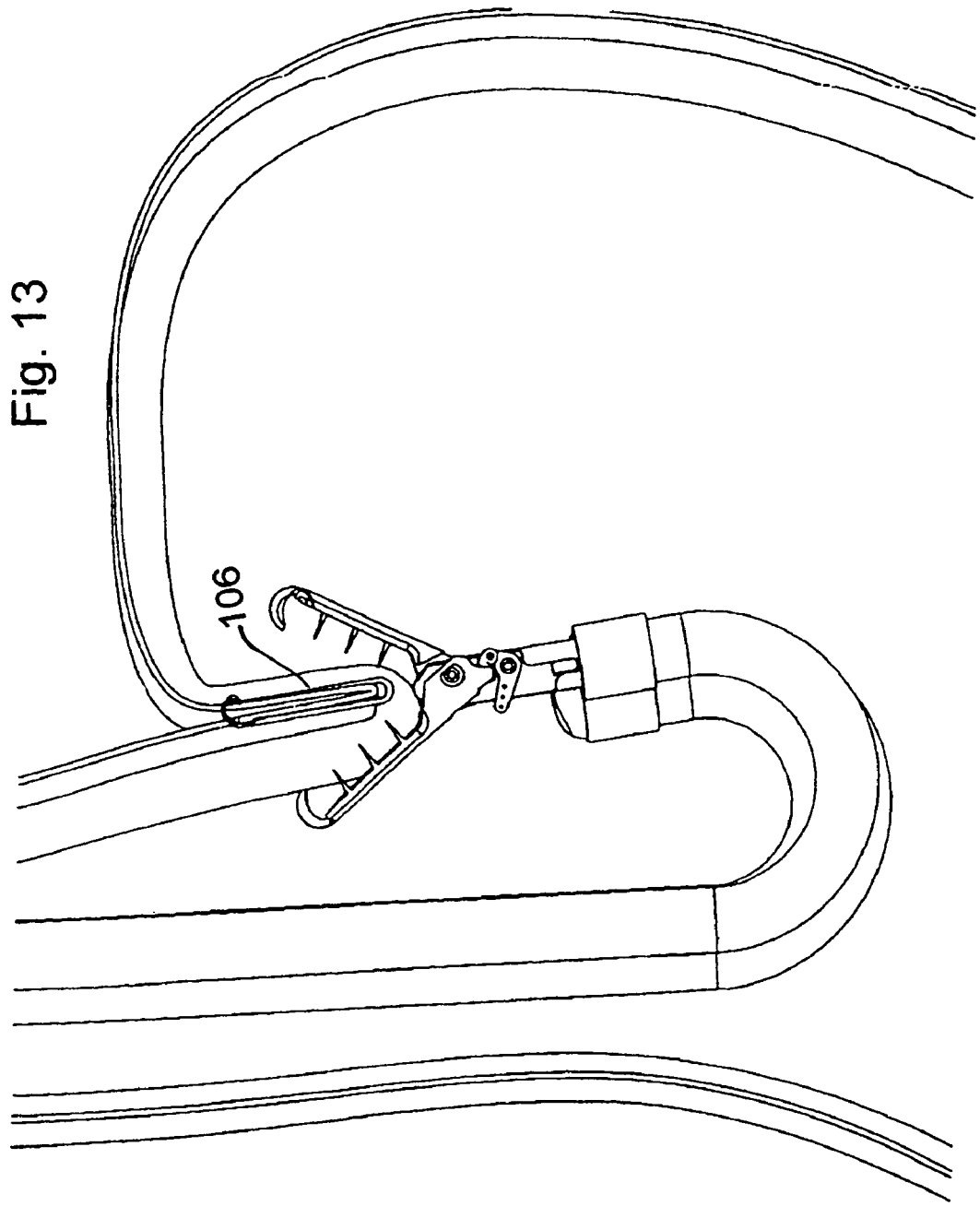
Figure 14:
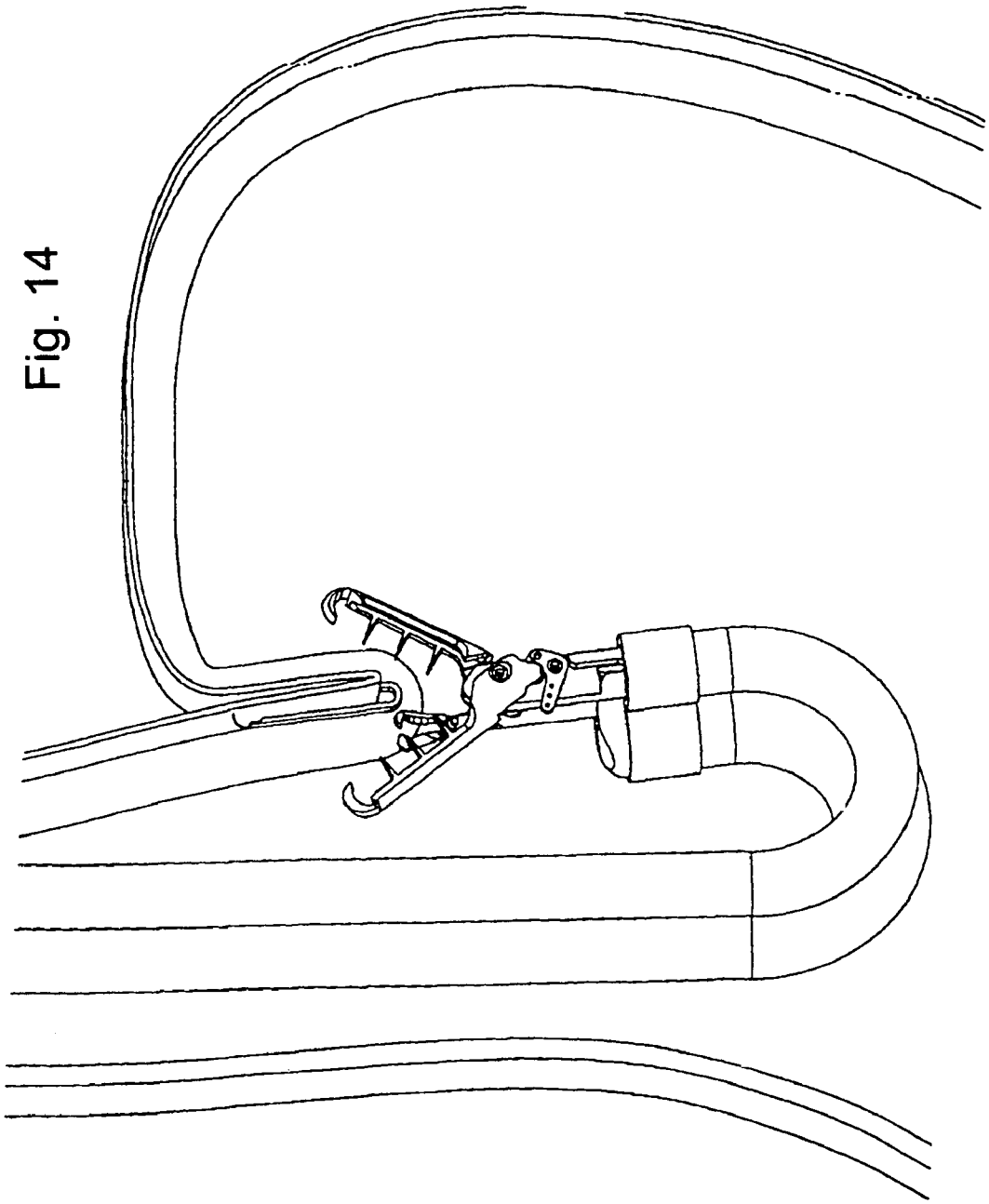

After the clip 106 is applied, the jaws of the clip applier are opened as shown in FIG. 13 and the clip 106 remains in place and plicates the fundus. Depending on the location of the clip and the nature of the patient's condition, a single clip may be sufficient. If other clips are deemed desirable by the practitioner, the clip applier is removed and re-loaded with another clip. After re-delivering the clip applier, the procedure may be repeated at another location as shown in FIG. 14. Given the size of the clips of the invention, anywhere from 1-4 clips will typically be used.

According to one aspect of the invention, the medial teeth on the jaws of the clip applier are long enough and sharp enough to damage the fundus sufficiently such that when the fundus heals adhesion occurs, binding the plicated fundus to the extent that the clip may no longer be needed. Thus, preferably, the teeth are long enough to pierce all layers of the fundus.

From the foregoing, those skilled in the art will appreciate that the methods of the invention may be performed with different types of graspers. In particular, alternative grasping devices such as a "cork screw" grasper can be used in conjunction with the clip applier of the invention to perform the methods of the invention.

It will also be appreciated that the clip applier of the invention may be attached to an endoscope in other ways as described in previously incorporated application Ser. No. 09/931,528, filed Aug. 16, 2001, entitled "Methods and Apparatus for Delivering a Medical Instrument Over an Endoscope while the Endoscope is in a Body Lumen".

As mentioned above, the clip applier of the invention has an outside diameter of approximately 6 mm. As shown in FIGS. 10-14, the clip applier is used in conjunction with an endoscope having an outside diameter of approximately 12 mm. To accommodate the clip applier, an exterior working channel having an exterior diameter of approximately 7 mm is optionally coupled to the endoscope as described in the previously incorporated co-owned application Ser. Nos. 09/931,528 and 60/292,419.

Figure 15:
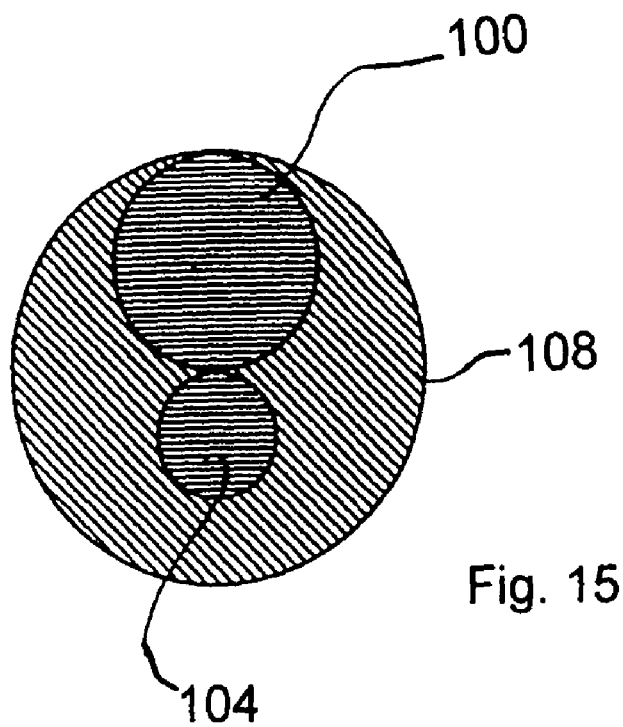
FIG. 15 is a diagram illustrating the comparative cross-section of the instruments used in the method illustrated in FIGS. 5-10 and a typical prior art instrument.

FIG. 15 is a scale representation of the cross-sectional area of the 12 mm endoscope 100 with the attached external 7 mm working channel 104, shown in horizontal shading. The cross sectional area of a prior art device 108 having an exterior diameter of approximately 24 mm is shown in diagonal shading. From FIG. 15, it will be appreciated that the methods and apparatus of the invention allow for a substantially smaller device which is more easily delivered transorally and which is more easily manipulated. The overall cross-sectional area of the apparatus of the invention is approximately 152 mm$^2$ as compared to the 314 mm$^2$ of the prior art devices.

Figure 16:
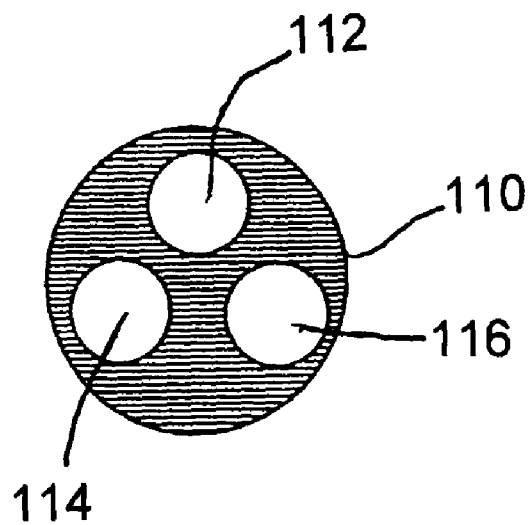
FIG. 16 is a cross-sectional view of a dual lumen endoscope which can be used in performing the methods of the invention.

As mentioned, the clip applier of the invention may also be used with a dual lumen endoscope. FIG. 16 is a scale representation of a dual lumen endoscope 110 having an optical lumen 112 and two 6 mm working lumina 114, 116. As compared to the device 108 in FIG. 15, the endoscope 110 has a substantially smaller cross-sectional area than the prior art device.

The clips used by the clip applier of the invention are substantially longer than the clips described in the previously incorporated co-owned applications, Ser. No. 09/891,775 and the simultaneously filed application, which are approximately 7 mm in length and adequate for general surgical applications. The retainer portion of the clips of the present invention are substantially longer in order to assure that all of the layers of the fundus are punctured.

Figure 17:
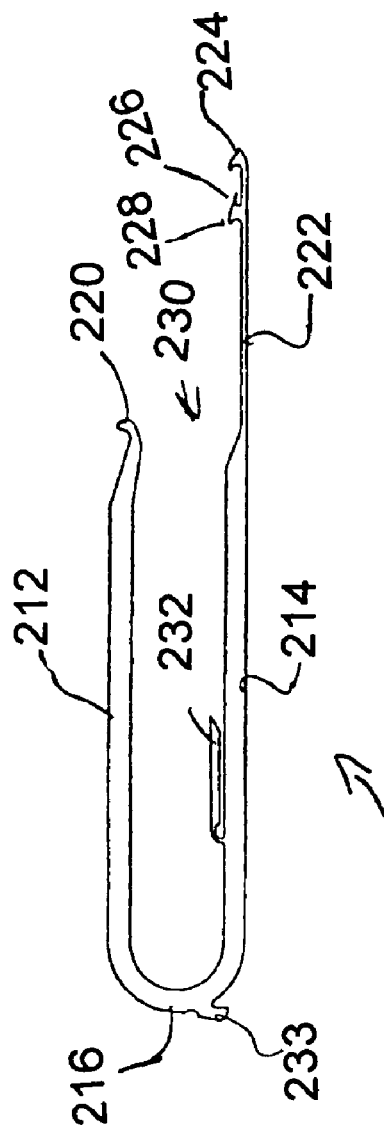
FIG. 17 is a side elevational view of a first embodiment of a clip according to the invention prior to application.
Figure 18:
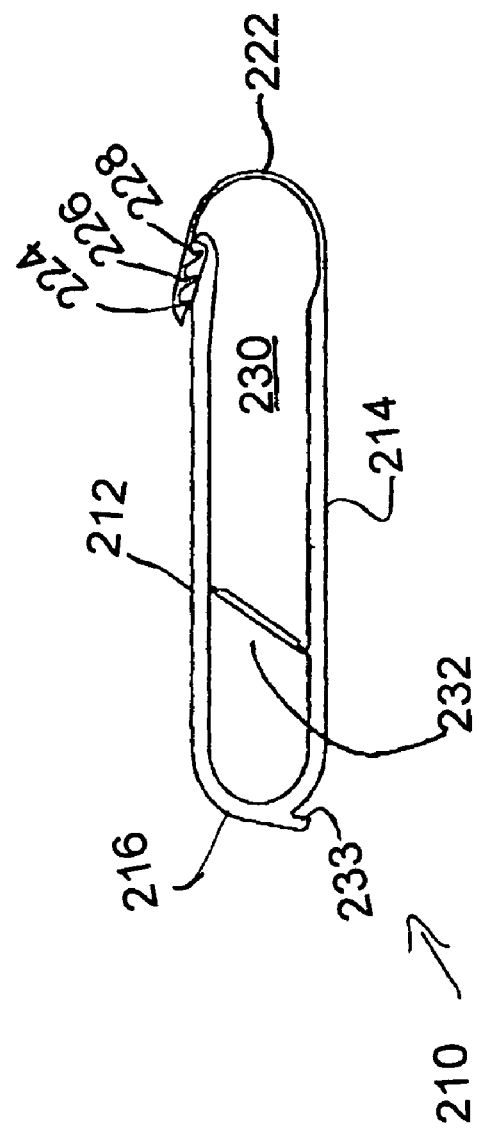
FIG. 18 is a side elevational view of the clip of FIG. 17 after application.

Turning now to FIGS. 17 and 18, a first embodiment of a surgical clip 210 according to the invention includes first and second arms 212, 214, respectively, and a bridge portion 216 therebetween such that the arms and bridge portion are in a generally U-shaped configuration. The first arm 12 is provided with an end catch 220, and the second arm 214 extends (or transitions) into a deformable retainer 222 having a tissue piercing tip 224 and a plurality of catch engagements, e.g. 226, 228. The arms define an open space 230 between them. The clip 210 is preferably made from a unitary piece of titanium, titanium alloy, stainless steel, tantalum, platinum, other high Z (substantially radiopaque) materials, nickel-titanium alloy, martensitic alloy, or plastic, although other suitable biocompatible materials may be used. The first and second arms 212, 214, as well as the bridge portion 216 are relatively stiff and not plastically deformable within the limits of force applied to the arms during use, while the retainer 222 is relatively easily plastically deformable by the clip applier.

Referring now to FIGS. 2-4 and 17-18, when the clip 210 is pushed forward in the clip applier with the jaws 22, 24 of the clip applier closed, the retainer 222 is bent across the opening 230 between the first and second arms 212, 214 and into engagement with the end catch 220 of the first arm 212 as shown in FIG. 18. The anvil formed by the grooves on the interior of the hooks 46, 48 of the clip applier jaws guide the bending of the retainer 222 causing it to puncture the fundus and couple to the end catch 220.

The clip 210 shown in FIGS. 17 and 18 is provided with an optional bendable barb 232 which provides a secondary stabilizing fixation point which helps keep the clip from rotating. As the clip is pushed forward over the fundus, tissue catches the barb 232 and bends it as shown in FIG. 18.

The clip 210 is also provided with an ear 233 on the bridge 216. The ear is used by the pushing mechanism (not shown) to grasp the end of the clip when it is loaded into the clip applier.

A second embodiment of a clip 310 according to the invention is shown in FIGS. 19 and 20. The clip 310 has two arms 312, 314 connected by a bridge 316. Both arms terminate in retainers 320, 322, each having a sharp end 321, 323. The clip 310 is also provided with a pair of ears 333, 335 on the bridge 316. The ears are used by the pushing mechanism (not shown) to grasp the end of the clip when it is loaded into the clip applier. This embodiment is intended for use with a clip applier having hooks with interior grooves which diverge, or which are in parallel planes. With reference to FIGS. 2-4 and 15-16, when the clip 310 is pushed forward, the retainer 320 is bent by the groove inside the hook 46 and the retainer 322 is bent by the groove inside the hook 48 to the configuration shown in FIG. 20. From FIG. 20, it will be appreciated that each retainer punctures the fundus twice substantially forming a circular fastener. Thus, it will also be appreciated that the retainers 320, 322 are significantly longer than the retainer 222 shown in FIGS. 17 and 18 and preferably are of a length at least n times the distance between the arms 312, 314. Insofar as the retainers 320, 322 each form a complete fastener, the function of the arms 312, 314 and the bridge 316 may be considered redundant.

FIGS. 21-23 illustrate a third embodiment of a clip 410 according to the invention. The clip 410 is similar to the clip 310 (with similar reference numerals increased by 100 referring to similar parts) except that the retainers 420, 422 are removable from the arms 412, 414. The arms 412, 414 terminate in female couplings 413, 415 which receive ends of the retainers 420, 422 in a slight interference fit. The clip 410 is also provided with a pair of ears 433, 435 on the bridge 416. The ears are used by the pushing mechanism (not shown) to grasp the end of the clip when it is loaded into the clip applier. The clip 410 is applied to the fundus in substantially the same way as described above with reference to the clip 310. However, after the retainers 420, 422 are bent by the anvils and the jaws are opened, the clip 410 is not released from the clip applier and the retainers are separated from the arms 412, 414. The resulting fastener formed by the retainers 420, 422 is shown in FIG. 23. This is actually two substantially parallel "b" shaped fasteners. Thus, it may only be necessary to apply a single retainer as shown in FIG. 24, for example.

Figure 25:
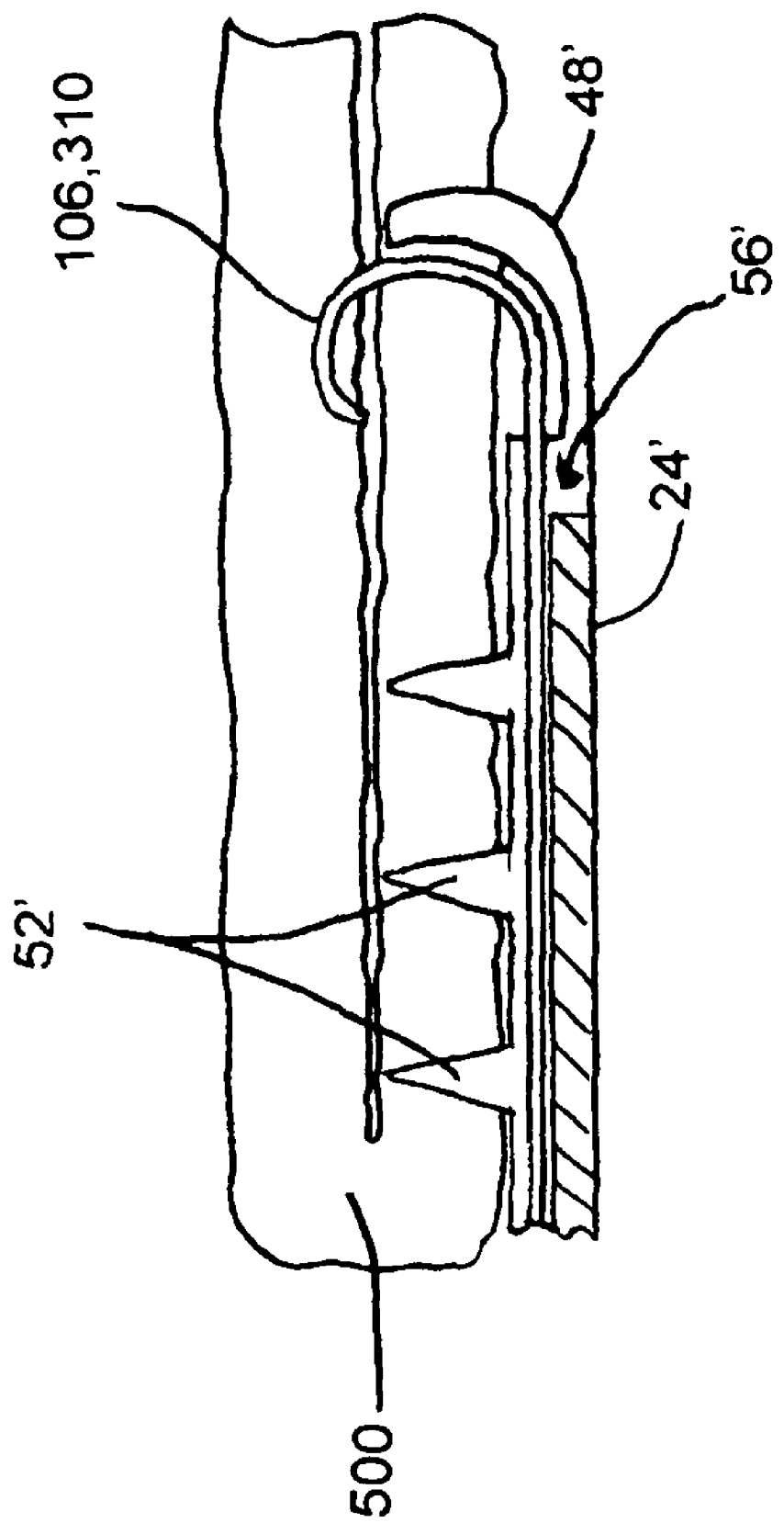
FIG. 25 is a fragmentary, cross-sectional enlarged view of a portion of the clip applier of FIG. 5 with a portion of a clip in an applier groove and through tissue.

FIG. 25 illustrates an enlarged portion of the clip applier of FIG. 5 showing that the clip 310 rests inside an applier groove 54', 56' and is bent by the anvil 48' as it pierces a folded over portion of body tissue 500.

There have been described and illustrated herein several embodiments of methods and apparatus for the endoluminal treatment of gastroesophageal reflux disease. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its spirit and scope as so claimed.

The invention claimed is:

1. An endoscopic surgical assembly, comprising:
a surgical clip; and
an endoscopic surgical instrument having:
   a hollow member having a proximal end and a distal end;
   a clevis coupled to said distal end of said hollow member and having an axle extending therefrom;
   an end effector rotatably coupled to said clevis and operable to apply said surgical clip to a location;
   a pull/push wire extending through said hollow member to said proximal end of said hollow member;
   a dual linkage having:
      a first element rotatably coupled directly to said axle and directly coupled to said pull/push wire; and
      a second element rotatably coupled to said first element and rotatably coupled to said end effector; and
   actuation means coupled to said proximal end of said hollow member and to said proximal end of said pull/push wire for moving said pull/push wire through said hollow member to cause a rotation of said end effector about said clevis.

2. The assembly according to claim 1, wherein:
said first element is L-shaped; and
said second element is coupled to said end effector distal of said axle.

3. The assembly according to claim 1, wherein:
said end effector has two jaws pivotally coupled to said clevis for applying said surgical clip to the location; and
at least one of said jaws is coupled to said second element and pivots at said clevis when said actuation means is actuated.

4. The assembly according to claim 1, wherein:
said end effector has first and second jaws pivotally coupled to said clevis for applying said surgical clip to the location;
said dual linkage is a first dual linkage;
said first jaw is coupled to said second element of said first dual linkage and pivots at said clevis when said actuation means is actuated; and further comprising:
a second pull/push wire extending through said hollow member to said proximal end of said hollow member; and
a second dual linkage having:
   a third element rotatably coupled directly to said axle and directly coupled to said second pull/push wire; and
   a fourth element rotatably coupled to said third element and rotatably coupled to said second jaw such that said second jaw pivots at said clevis when said actuation means is actuated.

5. The assembly according to claim 4, wherein:
said first and third elements are L-shaped;
said first and third elements are coupled to a respective one of said pull/push wires proximal of said axle; and
said second and fourth elements are coupled to a respective one of said two jaws to pivot said jaws at said clevis when said actuation means is actuated.

6. The assembly according to claim 3, wherein said jaws are substantially identical.

7. The assembly according to claim 1, wherein said dual linkage is coupled to said clevis and to said end effector to amplify force applied from said pull/push wire to said end effector.

8. The assembly according to claim 1, wherein said dual linkage is coupled to said clevis and to said end effector to increase mechanical advantage as said end effector closes.

9. The assembly according to claim 3, wherein both of said jaws are provided with a plurality of teeth puncturing and damaging tissue adjacent two sides of the surgical clip when said jaws are closed on the tissue.

10. The assembly according to claim 3, wherein:
at least one of said jaws has:
a clip guiding channel shaped to fit said surgical clip, said clip guiding channel having an end; and
a hook shaped anvil at said end of said clip guiding channel; and
said jaws apply said surgical clip with said clip guiding channel.

11. The assembly according to claim 10, wherein said anvil has at least one of a helical surface and a curved surface.

12. The assembly according to claim 11, wherein said at least one surface is curved about a single axis.

13. The assembly according to claim 10, wherein:
each of said jaws has a longitudinal axis and a vertical axis perpendicular to said longitudinal axis, and
each of said channels is at an angle relative to said vertical axis.

14. The assembly according to claim 1, wherein said clevis and said end effector have a maximum outside diameter of approximately 6 mm.

15. The assembly according to claim 1, wherein said clevis and said end effector have an overall maximum cross-sectional area of approximately 152 $mm^2$.

16. An endoscopic surgical assembly, comprising:
a surgical clip; and
an endoscopic surgical instrument having:
a hollow member having a proximal end and a distal end;
a clevis coupled to said distal end of said hollow member and having an axle extending therefrom;
an end effector rotatably coupled to said clevis and operable to apply said surgical clip to a location;
a pull/push wire extending through said hollow member to said proximal end of said hollow member;
a dual linkage having:
a first element rotatably coupled directly to said axle and directly coupled to said pull/push wire; and
a second element rotatably coupled to said first element and rotatably coupled to said end effector; and
an actuator coupled to said proximal end of said hollow member and to said proximal end of said pull/push wire for moving said pull/push wire through said hollow member to cause a rotation of said end effector about said clevis.

17. The assembly according to claim 16, wherein:
said first element is L-shaped; and
said second element is coupled to said end effector distal of said axle.

18. The assembly according to claim 16, wherein:
said end effector has two jaws pivotally coupled to said clevis for applying said surgical clip to the location; and
at least one of said jaws is coupled to said second element and pivots at said clevis when said actuator is actuated.

19. The assembly according to claim 16, wherein:
said end effector has first and second jaws pivotally coupled to said clevis for applying said surgical clip to the location;
said dual linkage is a first dual linkage;
said first jaw is coupled to said second element of said first dual linkage and pivots at said clevis when said actuator is actuated; and further comprising:
a second pull/push wire extending through said hollow member to said proximal end of said hollow member; and
a second dual linkage having:
a third element rotatably coupled directly to said axle and directly coupled to said second pull/push wire; and
a fourth element rotatably coupled to said third element and rotatably coupled to said second jaw such that said second jaw pivots at said clevis when said actuator is actuated.

20. The assembly according to claim 19, wherein:
said first and third elements are L-shaped;
said first and third elements are coupled to a respective one of said pull/push wires proximal of said axle; and
said second and fourth elements are coupled to a respective one of said two jaws to pivot said jaws at said clevis when said actuator is actuated.

21. The assembly according to claim 18, wherein said jaws are substantially identical.

22. The assembly according to claim 16, wherein said dual linkage is coupled to said clevis and to said end effector to amplify force applied from said pull/push wire to said end effector.

23. The assembly according to claim 16, wherein said dual linkage is coupled to said clevis and to said end effector to increase mechanical advantage as said end effector closes.

24. The assembly according to claim 18, wherein both of said jaws are provided with a plurality of teeth puncturing and damaging tissue adjacent two sides of the surgical clip when said jaws are closed on the tissue.

25. The assembly according to claim 18, wherein:
at least one of said jaws has:
a clip guiding channel shaped to fit said surgical clip, said clip guiding channel having an end; and
a hook shaped anvil at said end of said clip guiding channel; and
said jaws apply said surgical clip with said clip guiding channel.

26. The assembly according to claim 25, wherein said anvil has at least one of a helical surface and a curved surface.

27. The assembly according to claim 26, wherein said at least one surface is curved about a single axis.

28. The assembly according to claim 25, wherein:
each of said jaws has a longitudinal axis and a vertical axis perpendicular to said longitudinal axis, and
each of said channels is at an angle relative to said vertical axis.

29. The assembly according to claim 16, wherein said clevis and said end effector have a maximum outside diameter of approximately 6 mm.

30. The assembly according to claim 16, wherein said clevis and said end effector have an overall maximum cross-sectional area of approximately 152 $mm^2$.

31. An endoscopic surgical assembly, comprising:
a surgical clip; and
an endoscopic surgical instrument having:
a hollow member having a proximal end and a distal end;
a clevis coupled to said distal end of said hollow member and having an axle extending therefrom;
an end effector rotatably coupled to said clevis and operable to apply said surgical clip to a location;
a pull/push wire extending through said hollow member to said proximal end of said hollow member;

a dual linkage including at least one element rotatably coupled directly to said axle, directly to said pull/push wire, and to said end effector, said dual linkage providing mechanical advantage in rotating said end effector to apply said surgical clip to the location; and actuation means coupled to said proximal end of said hollow member and to said proximal end of said pull/push wire for moving said pull/push wire through said hollow member to cause a rotation of said end effector about said clevis.

32. An endoscopic surgical assembly, comprising:
a surgical clip; and
an endoscopic surgical instrument having:
   a hollow member having a proximal end and a distal end;
   a clevis coupled to said distal end of said hollow member and having an axle extending therefrom;
   an end effector rotatably coupled to said clevis and operable to apply said surgical clip to a location;
   a pull/push wire extending through said hollow member to said proximal end of said hollow member;
   a dual linkage including at least one element rotatably coupled directly to said axle, directly to said pull/push wire, and to said end effector, said dual linkage providing mechanical advantage in rotating said end effector to apply said surgical clip to the location; and
   an actuator coupled to said proximal end of said hollow member and to said proximal end of said pull/push wire for moving said push/pull wire through said hollow member to cause a rotation of said end effector about said clevis.

* * * * *